(12) United States Patent
Yamamoto et al.

(10) Patent No.: US 10,006,011 B2
(45) Date of Patent: *Jun. 26, 2018

(54) POLYPEPTIDE CONTAINING DNA-BINDING DOMAIN

(71) Applicant: HIROSHIMA UNIVERSITY, Higashihiroshima-shi, Hiroshima (JP)

(72) Inventors: Takashi Yamamoto, Kure (JP); Tetsushi Sakuma, Higashihiroshima (JP); Hiroshi Ochiai, Higashihiroshima (JP); Shinya Matsuura, Hiroshima (JP); Tatsuo Miyamoto, Hiroshima (JP)

(73) Assignee: Hiroshima University, Hiroshima (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/019,630

(22) Filed: Feb. 9, 2016

(65) Prior Publication Data

US 2016/0152990 A1    Jun. 2, 2016

Related U.S. Application Data

(63) Continuation-in-part of application No. 14/911,154, filed as application No. PCT/JP2014/062518 on May 9, 2014.

(30) Foreign Application Priority Data

Aug. 9, 2013  (JP) .................. 2013-166768

(51) Int. Cl.
C12N 9/22      (2006.01)
C12N 15/63     (2006.01)
C40B 40/08     (2006.01)

(52) U.S. Cl.
CPC ............... *C12N 9/22* (2013.01); *C12N 15/63* (2013.01); *C40B 40/08* (2013.01); *C07K 2319/80* (2013.01)

(58) Field of Classification Search
None
See application file for complete search history.

(56) References Cited

U.S. PATENT DOCUMENTS

| | | | |
|---|---|---|---|
| 2011/0239315 A1 | 9/2011 | Bonas et al. | |
| 2011/0301073 A1* | 12/2011 | Gregory ............. | C12N 15/62 514/1.1 |
| 2013/0117869 A1* | 5/2013 | Duchateau ............ | C12N 9/22 800/13 |

FOREIGN PATENT DOCUMENTS

| | | |
|---|---|---|
| JP | 2013-094148 A | 5/2013 |
| JP | 2013-529083 A | 7/2013 |
| WO | 2011/072246 | 6/2011 |
| WO | 2011/146121 A1 | 11/2011 |
| WO | 2011/154393 A1 | 12/2011 |
| WO | 2011/159369 A1 | 12/2011 |
| WO | 2012/093833 A2 | 7/2012 |

OTHER PUBLICATIONS

Sander et al., Targeted gene disruption in somatic zebrafish cells using engineered TALENs, Nature Biotechnology, 19: 697- 698 (2011); Supplementary materials.*
Sakuma et al., "Advanced methods for the construction, evaluation and application of TALENs," Joint Meeting of the 45th Annual Meeting of the Japanese Society of Developmental Biologists & the 64th Annual Meeting of the Japan Society for Cell Biology, Program & Abstracts, JYSS2-22: 303 (2012).
Sakuma et al., "Platinum Gate TALEN: Establishment of highly-active TALEN construction system," Dai 46 Kai Japanese Society of Developmental Biologists Yokoshu (2013).
Ota et al., "Efficient identification of TALEN-mediated genome modifications using heteroduplex mobility assays," Genes to Cells, 18: 450-458 (2013).
Miller et al., "A TALE nuclease architecture for efficient genome editing," Nature Biotechnology, 29: 143-150 (2011).
Gaj et al., "ZFN, TALEN, and CRISPR/Cas-based methods for genome engineering," Trends in Biotechnology, 31: 397-405 (2013).
Cermak et al., "Efficient design and assembly of custom TALEN and other TAL effector-based constructs for DNA targeting," Nucleic Acids Research, 39: e82 (2011).
Boch et al., "Xanthomonas AvrBs3 Family-Type III Effectors: Discovery and Function," Annual Review of Phytopathology, 48: 419-436 (2010).
Sakuma et al., "Repeating pattern of non-RVD variations in DNA-binding modules enhances TALEN activity," Scientific Reports, 3: 3379 (2013).
Mussolino et al., "A novel TALE nuclease scaffold enables high genome editing activity in combination with low toxicity," Nucleic Acids Research, 39: 9283-9293 (2011).
Sander et al., Targeted gene disruption in somatic zebrafish cells using engineered TALENs, Nature Biotechnology, 29: 697-698 (2011).
Bedell et al., "In vivo genome editing using a high-efficiency TALEN system," Nature, 491: 114-120 (2012).
Sakuma et al., "Efficient TALEN construction and evaluation methods for human cell and animal applications," Genes to Cells, 18: 315-326 (2013).
Soldner et al., "Generation of Isogenic Pluripotent Stem Cells Differing Exclusively at Two Early Onset Parkinson Point Mutations," Cell, 146: 318-331 (2011).

(Continued)

*Primary Examiner* — Addison D Ault
(74) *Attorney, Agent, or Firm* — Morgan, Lewis & Bockius LLP

(57) ABSTRACT

The present invention provides an artificial nuclease comprising a DNA-binding domain and a function domain linked to each other via a polypeptide consisting of 35 to 55 amino acid residues wherein amino acid residues at two sites in a DNA-binding module contained in a DNA-binding domain exhibit a mode of repetition that is different for every four DNA-binding modules; a vector for expressing said artificial nuclease; a vector library for preparing said vector; and a vector set for preparing said vector library.

20 Claims, 10 Drawing Sheets

(56) References Cited

OTHER PUBLICATIONS

Translation of International Preliminary Report on Patentability issued in related International Patent Application No. PCT/JP2014/062518 dated Feb. 11, 2016.
International Search Report issued in related International Patent Application No. PCT/JP2014/062518 dated Aug. 12, 2014.
Office Action issued in related Japanese Patent Application No. 2013-166768 dated Sep. 8, 2015.
Office Action issued in related Japanese Patent Application No. 2013-166768 dated Jan. 26, 2016.
Office Action issued in U.S. Appl. No. 14/911,154 dated Oct. 17, 2016.
Office Action issued in U.S. Appl. No. 14/911,154 dated Feb. 7, 2017.
Miller et al., "A TALE nuclease architecture for efficient genome editing," Nature Biotechnology, 29: 143-150 (2011) (supplementary information).
Mussolino et al., "A novel TALE nuclease scaffold enables high genome editing activity in combination with low toxicity," Nucleic Acids Research, 39: 9283-9293 (2011) (supplementary figure & supplementary table).
Bedell et al., "In vivo genome editing using a high-efficiency TALEN system," Nature, 491: 114-120 (2012) (supplementary information).

* cited by examiner

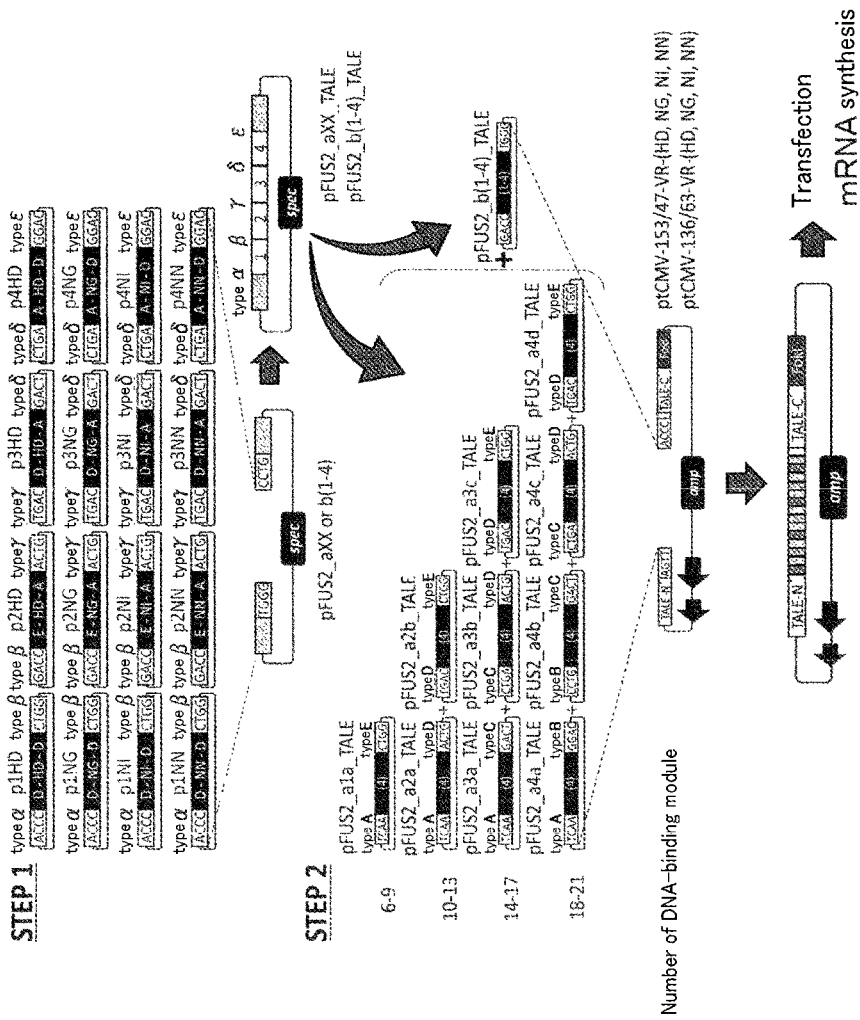
[Fig. 1]

[Fig. 2]

>p1HD (SEQ ID NO: 1 and 2)
CTGACCCCGGACCAGGTGGTTGCAATCGCTTCACACGATGGGGGAAAGCAGGCCCTAGAAACCGTTCAGCGACTCCTGCCCGTCCTGTGCCAGGACCACGGC
 L  T  P  D  Q  V  V  A  I  A  S  H  D  G  G  K  Q  A  L  E  T  V  Q  R  L  L  P  V  L  C  Q  D  H  G >p1NG (SEQ ID NO: 3 and 4)
CTGACCCCCGACCAGGTTGTCGCTATTGCTAGTAACGGCGGAAAGCAGGCCCTGGAAACAGTTCAGCGCCTCTTGCCGGTCTTGTGTCAGGACCACGGC
 L  T  P  D  Q  V  V  A  I  A  S  N  G  G  K  Q  A  L  E  T  V  Q  R  L  L  P  V  L  C  Q  D  H  G >p1NI (SEQ ID NO: 5 and 6)
CTGACCCCAGACCAGGTTGTGGCCATCGCCAGCAACATAGGTGCAAGCAGGCCCTCGAAACCGTCCAGAGACTGTTACCGGTTCTCTGCCAGGACCACGGC
 L  T  P  D  Q  V  V  A  I  A  S  N  I  G  G  K  Q  A  L  E  T  V  Q  R  L  L  P  V  L  C  Q  D  H  G >p1NN (SEQ ID NO: 7 and 8)
CTGACCCCAGACCAAGTTGTCGCGATTGCAAGCAACAACGGAGCAAACAAGCCTTAGAAACAGTCCAGAGATTGTTGCCGGTGCTGTGCCAAGACCACGGC
 L  T  P  D  Q  V  V  A  I  A  S  N  N  G  G  K  Q  A  L  E  T  V  Q  R  L  L  P  V  L  C  Q  D  H  G >p2HD (SEQ ID NO: 9 and 10)
CTGACCCCCGGAACCAGGTGGTTGCAATCGCGTTCACACGATGGGGGAAAGCAGGCCCTAGAAACCGTTCAGCGACTCCTGCCCGTCCTGTGCCAGGCCCACGGC
 L  T  P  E  Q  V  V  A  I  A  S  H  D  G  G  K  Q  A  L  E  T  V  Q  R  L  L  P  V  L  C  Q  A  H  G >p2NG (SEQ ID NO: 11 and 12)
CTGACCCCCGAACCAGGTTGTCGCTATTGCTAGTAACGGCGGAGAACAGGCGCTGGAAACAGGCCAAACAGGCCCTGGAAACAGTTCAGCGGCCCTCTTGCCGGTCTTGTGTCAGGCCCACGGC
 L  T  P  E  Q  V  V  A  I  A  S  N  G  G  K  Q  A  L  E  T  V  Q  R  L  L  P  V  L  C  Q  A  H  G >p2NI (SEQ ID NO: 13 and 14)
CTGACCCCAGAACCAGGTTGTGGCCATCGCCAGCAACATAGGTGGCAAGCAGGCCCTCGAAACCGTCCAGAGACTGTTACCGGTTCTCTGCCAGGCCCACGGC
 L  T  P  E  Q  V  V  A  I  A  S  N  I  G  G  K  Q  A  L  E  T  V  Q  R  L  L  P  V  L  C  Q  A  H  G >p2NN (SEQ ID NO: 15 and 16)
CTGACCCCAGAACCAAGTTGTCGCGATTGCAAGCAACAACGGAGCAAACAAGCCTTAGAAACAGTCCAGAGATTGTTGCCGGTGCTGTGCCAAGCCCACGGC
 L  T  P  E  Q  V  V  A  I  A  S  N  N  G  G  K  Q  A  L  E  T  V  Q  R  L  L  P  V  L  C  Q  A  H  G

[Fig. 2 cont.]

>p3HD (SEQ ID NO: 17 and 18)
CTGACCCCGGACCAGTGGTTGCAATCGGTCACACGATGGGGAAAGCAGGCCCTAGAAACCGTTCAGCGACTCCTGCCGGTCCTGTGCCAGGCCCACGGC
 L  T  P  D  Q  V  V  A  I  A  S  H  D  G  G  K  Q  A  L  E  T  V  Q  R  L  L  P  V  L  C  Q  A  H  G >p3NG (SEQ ID NO: 19 and 20)
CTGACCCCCGACCAGGTTGTCGGTTATTGCTAGTAACGCGGAGGCAAACAGGCGCTGAAACAGTTCAGCGCCTCTTGCCGGTCTTGTGTCAGGCCCACGGC
 L  T  P  D  Q  V  V  A  I  A  S  N  G  G  G  K  Q  A  L  E  T  V  Q  R  L  L  P  V  L  C  Q  A  H  G >p3NI (SEQ ID NO: 21 and 22)
CTGACCCCAGACCCAGGTGTGGCCATCGCCAGCAACATAGGTGGCAAGCAGGCCCTCGAAACCGTCCAGAGACTGTTACCGGTTCTCTGCCAGGCCCACGGC
 L  T  P  D  Q  V  V  A  I  A  S  N  I  G  G  K  Q  A  L  E  T  V  Q  R  L  L  P  V  L  C  Q  A  H  G >p3NN (SEQ ID NO: 23 and 24)
CTGACCCCAGACCAAGTTGTCGCGATTGCAAGCAACAACGGAGGCAAACAAGCCTTAGAAACAGTCCAGAGATTGTTGCCTGCTGTGCCAAGCCCACGGC
 L  T  P  D  Q  V  V  A  I  A  S  N  N  G  G  K  Q  A  L  E  T  V  Q  R  L  L  P  V  L  C  Q  A  H  G >p4HD (SEQ ID NO: 25 and 26)
CTGACCCCGGCCCAGGTGGTTGCAATCGCTTCACACGATGGGGAAAGCAGGCCCTAGAAACCGTTCAGCGACTCCTGCCGGTCCTGTGCCAGGACCACGGC
 L  T  P  A  Q  V  V  A  I  A  S  H  D  G  G  K  Q  A  L  E  T  V  Q  R  L  L  P  V  L  C  Q  D  H  G >p4NG (SEQ ID NO: 27 and 28)
CTGACCCCGCCCAGGTTGTCGCTATTGCTAGTAACGGCGGAGGCAAACAGGCGCTGGAAACAGTTCAGCGCCTCTTGCCGGTCTTGTGTCAGGACCACGGC
 L  T  P  A  Q  V  V  A  I  A  S  N  G  G  G  K  Q  A  L  E  T  V  Q  R  L  L  P  V  L  C  Q  D  H  G >p4NI (SEQ ID NO: 29 and 30)
CTGACCCCCCAGCCCAGGTCGTTGTGGCCATCGCCAGCAACATAGGTGGCAAGCAGGCCCTCGAAACCGTCCAGAGACTGTTACCGGTTCTCTGCCAGGACCACGGC
 L  T  P  A  Q  V  V  A  I  A  S  N  I  G  G  K  Q  A  L  E  T  V  Q  R  L  L  P  V  L  C  Q  D  H  G >p4NN (SEQ ID NO: 31 and 32)
CTGACCCCAGCCCAGGTCGCGATTGCGAGCAACAACGGAGGCAAACAAGCCTTAGAAACAGTCCAGAGATTGTTGCCGGTGCTGTGCCAAGACCACGGC
 L  T  P  A  Q  V  V  A  I  A  S  N  N  G  G  K  Q  A  L  E  T  V  Q  R  L  L  P  V  L  C  Q  D  H  G

[Fig. 3]

>HPRT1_R17 (+153/+47) scaffold - Variable repeat)    (SEQ ID NO: 33 and 34)

```
ATGGCTTCCTCCCTCCAAAGAAAAGAGAAGTTGCGGCCGCTGACTACAAGGATGACGACGATAAAGTTGGAAGGACGCAAGTGGTTGGTCTAGAA    < 100
 M  A  S  S  P  P  K  K  K  R  K  V  A  A  A  A  D  Y  K  D  D  D  D  K  S  W  K  D  A  S  G  W  S  R  M

TGCATGCGGCCCCGCGACGTGCTGCGCACCCTCGGCTACAGCCAGCAGCAGGAGCATGCGGCCCCGCGACGTCGGCTACAGCCAGCAGCAGGAGCAAGA    < 200
 H  A  P  R  R  R  A  A  Q  P  S  D  A  S  P  A  A  Q  V  D  L  R  T  L  G  Y  S  Q  Q  Q  E

GAAGATCAAAACCGAAGTGCGTTCGACAGTGGCTCGCAGGAGCACATCGTTGCGCTCAGCCAACAC    < 300
 K  I  K  P  K  V  R  S  T  V  A  Q  H  H  E  A  L  V  G  H  G  F  T  H  A  H  I  V  A  L  S  Q  H

CCGGCAGCCGTTAGGACCGTCGCTGTCACGTATCAGCATATAACGGCGTTGCAGAGGCAGACGAAGACATCGTTGGCGTCGGCAAACAGTGGT    < 400
 P  A  A  L  G  T  V  A  V  T  Y  Q  H  I  I  T  A  L  P  E  A  T  H  E  D  I  V  G  V  G  K  Q  W  S

CCGGCCACGCGCCTGAGGCCTTGCTGCTTACGGATGCGGGGGAGTTGAGAGGTCCGCGTTACAGTTGGACACAGGCCAACTGTGAAGATTGCAAAACG    < 500
 G  A  R  A  L  E  A  L  L  L  T  D  A  G  E  L  R  G  P  P  L  Q  L  D  T  G  Q  L  V  K  I  A  K  R

TGGCGGGTGACCGGTGCAGTGCATGGAGGCGCAATGCGCTCAACGGGAGCGCTCACCCTCAACTGACCCCCAGACCAGTTGGCCATGCCAGC    < 600
 G  G  V  T  A  M  E  A  V  H  R  N  A  L  T  G  A  P  L  N  L  T  P  D  Q  V  V  A  I  A  S

AACATAGGTGGCAAGCAGGCCCTCGAAACCGTCCAGAGACAGTTGCTGCCGCTCTTGCCGGGTTCTCCGGTTCAGGCCAGTTGCGGTATTGCTA    < 700
 N  I  G  G  K  Q  A  L  E  T  V  Q  R  L  L  P  V  L  C  Q  D  H  G  L  T  P  E  Q  V  V  A  I  A  S

GTAACGGCGGAGGCAAACAGGCGCTTGAGAACAGTTCAGCGCCTCTTGCCGCCTGTCAGGCCCAGACCAGGTTGTGGCCATCGC    < 800
 N  G  G  G  K  Q  A  L  E  T  V  Q  R  L  L  P  V  L  C  Q  D  H  G  L  T  P  D  Q  V  V  A  I  A

CAGCAACATAGTGGCAAGCAGGCCCTCGAAACCGTCCAGAGACAGTTGCTGCTCTGCCGCCTGTCAGGCCCAGGTTGTTGCAATC    < 900
 S  N  I  G  G  K  Q  A  L  E  T  V  Q  R  L  L  P  V  L  C  Q  A  H  G  L  T  P  A  Q  V  V  A  I

GCGTCACGATGGAAGCAGGCCCTCGAAACAGGCCCTCGAAAACCGTCCAGAGACAGTTGCTCCTGCCTGTGCCCTGAGTGCTCTGCTA    < 1000
 A  S  M  E  K  Q  A  L  E  T  V  Q  R  L  L  P  V  L  C  Q  D  H  G  L  T  P  D  Q  V  V  A  I

TTGCTAGTAACGGCGGAGGCAAACAGGCGCTTCAGGAACAGTTCAGCGACTCTTGTGCAGGACACTGGGTCTTGTGCCAGGTGTTGC    < 1100
 A  S  N  G  G  G  K  Q  A  L  E  T  V  Q  R  L  L  P  V  L  C  Q  D  D  H  G  L  T  P  E  Q  V  V  A

AATGGCGCCACACGATGGGGGACATAGTGGGCAAGCAGGCCCTAGAAACCGTTCAGCGACTCCTCGTCCGCTGCCAGGCCCACGCCCGGCCTGACCGCGGCCCAGTTGCC    < 1200
 I  A  S  H  D  G  G  K  Q  A  L  E  T  V  Q  R  L  L  P  V  L  C  Q  D  H  G  L  T  P  D  Q  V  V

GCCATCGCCCAGCAACATAGTGGCAAGCAGGCCCTCGAAGCGGCCCTCGAAACAGGTGTTCAGGGCCTTCTGCCAGGTGTTACCGGTTGCCAGGACTGTTACGGTTACCGCACCGGACCGAGT    < 1300
 A  I  A  Q  Q  A  H  G  L  T  P  A  Q  V  V  A  I  A  S  N  I  G  G  K  Q  A  L  E  T  V  Q  R  L  L  P  V  L  C  Q  A  H  G  L  T  P  A  Q  V  V

TTGCAATGCGGTGACAGATGGGACCGATGGGGAAAGCAGGGCAAAAGGCCAAAGCAGGCCCTCGAAGTGCAGACCCCAGACCTGATCCCTGAGCTGCCAGACCAGCCAGGT    < 1400
 A  I  A  S  H  D  G  G  K  Q  A  L  E  T  V  Q  R  L  L  P  V  L  C  Q  D  H  G  L  T  P  D  Q  V

TGTGGCCATCGCCAGCAACATAGGTGGCAAGCAGGCCCTGAAAACCGTCGTGCAGAGACTGTTACCGGTTCTGCTGCCAGTGTTCTCTGCCAGGACCCGGAACAG    < 1500
 V  A  I  A  S  N  I  G  G  K  Q  A  L  E  T  V  Q  R  L  L  P  V  L  C  Q  D  H  G  L  T  P  E  Q
```

[Fig. 3 cont.]

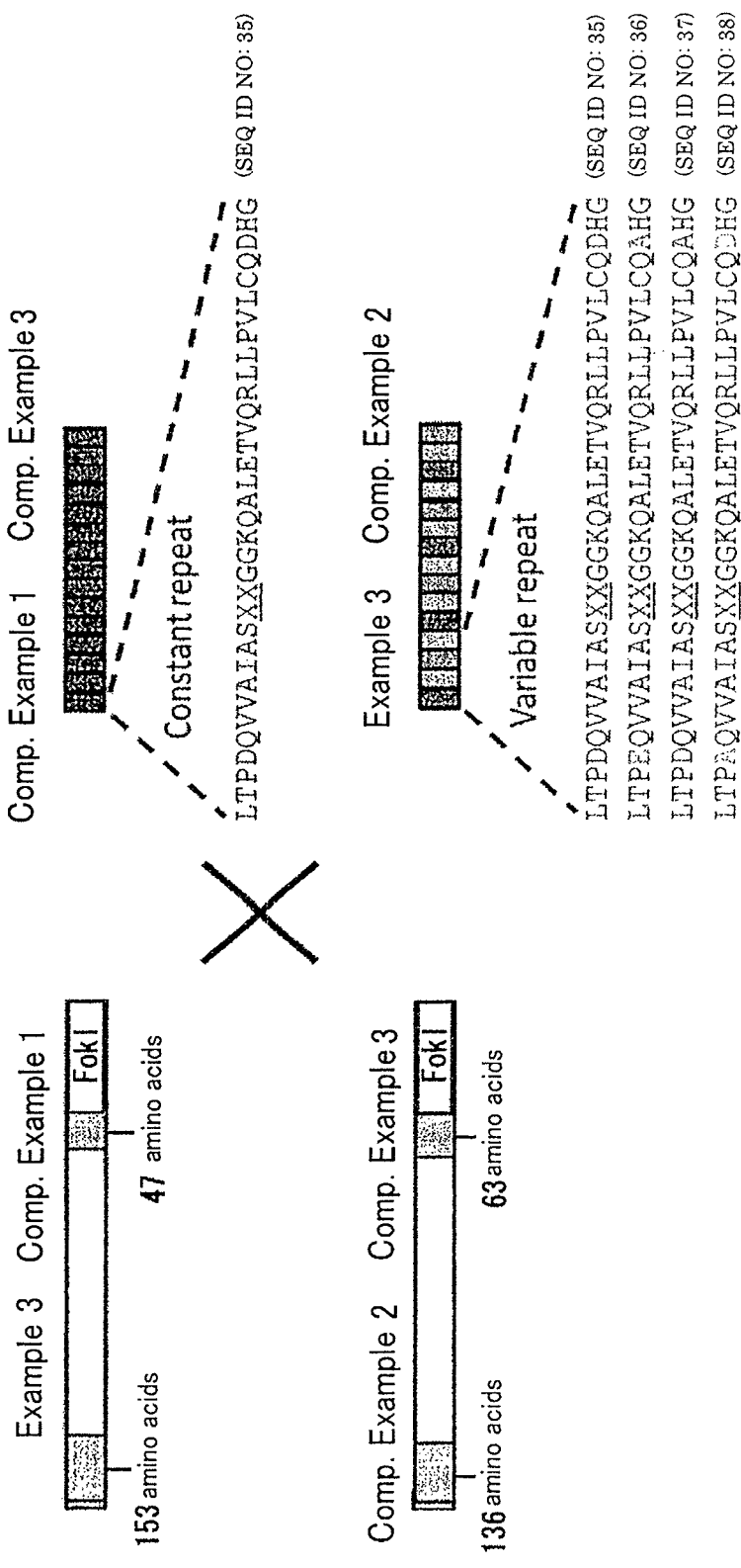

[Fig. 4B]
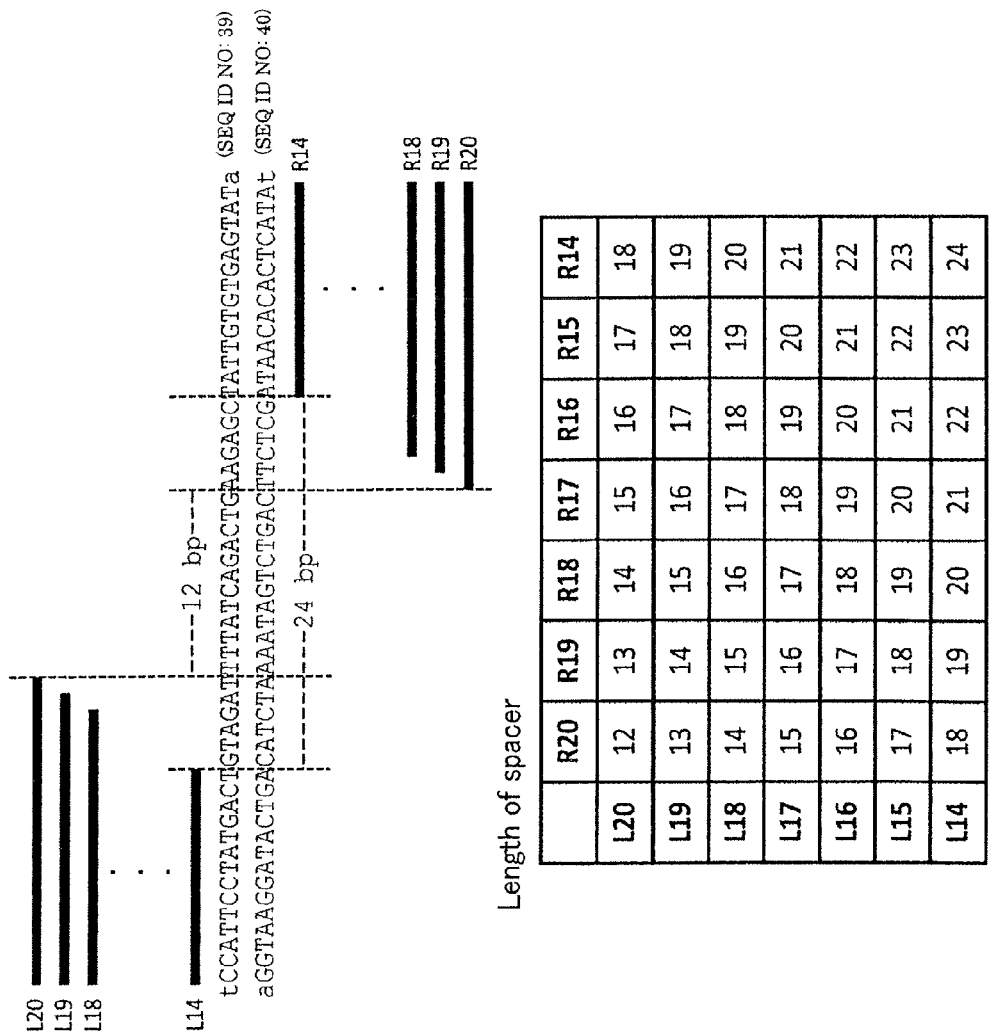

[Fig. 4C]

Comp. Example 1

|  | R20 | R19 | R18 | R17 | R16 | R15 | R14 |
|---|---|---|---|---|---|---|---|
| L20 | 2.38 | 2.833 | 2.92 | 1 | 0.9391 | 0.2425 | 0.1547 |
| L19 | 2.395 | 2.278 | 2.577 | 1.1063 | 0.891 | 0.2756 | 0.2179 |
| L18 | 1.977 | 2.736 | 2.292 | 1.5885 | 1.2708 | 0.3168 | 0.2177 |
| L17 | 1.069 | 1.318 | 1.399 | 1.3615 | 1.1249 | 0.622 | 0.2712 |
| L16 | 0.511 | 0.334 | 0.28 | 0.2319 | 0.6385 | 0.417 | 0.227 |
| L15 | 0.272 | 0.302 | 0.24 | 0.3546 | 0.8593 | 0.3231 | 0.2054 |
| L14 | 0.184 | 0.184 | 0.153 | 0.2064 | 0.5492 | 0.2588 | 0.2502 |

Example 3

|  | R20 | R19 | R18 | R17 | R16 | R15 | R14 |
|---|---|---|---|---|---|---|---|
| L20 | 2.445 | 2.501 | 1.858 | 1.1047 | 1.0078 | 0.6519 | 0.2197 |
| L19 | 2.733 | 2.305 | 2.004 | 1.0048 | 0.7188 | 0.5388 | 0.2186 |
| L18 | 1.176 | 1.162 | 1.286 | 0.7033 | 0.5497 | 0.562 | 0.3614 |
| L17 | 0.828 | 0.644 | 0.397 | 0.5341 | 0.6494 | 1.1601 | 0.633 |
| L16 | 0.215 | 0.225 | 0.183 | 0.2637 | 0.5494 | 0.7227 | 0.4889 |
| L15 | 0.272 | 0.246 | 0.257 | 0.7264 | 1.4315 | 1.077 | 0.6293 |
| L14 | 0.22 | 0.326 | 0.388 | 0.3808 | 0.7572 | 0.6039 | 0.2759 |

Comp. Example 3

|  | R20 | R19 | R18 | R17 | R16 | R15 | R14 |
|---|---|---|---|---|---|---|---|
| L20 | 0.3304 | 1.7026 | 1.3916 | 1.6539 | 2.1676 | 1.7166 | 1.1699 |
| L19 | 0.9829 | 2.3112 | 2.5703 | 2.3629 | 2.4137 | 2.1688 | 0.9308 |
| L18 | 1.1349 | 1.701 | 1.575 | 1.3959 | 1.8844 | 1.7326 | 2.0112 |
| L17 | 1.4697 | 1.7512 | 2.1577 | 2.4244 | 2.15 | 2.4187 | 2.8682 |
| L16 | 1.1714 | 0.9716 | 1.3691 | 1.0886 | 2.8059 | 2.6676 | 3.3866 |
| L15 | 1.3628 | 1.2337 | 1.378 | 0.8545 | 2.0986 | 1.6745 | 1.2354 |
| L14 | 1.126 | 1.6514 | 1.1774 | 1.0851 | 2.0518 | 1.3555 | 1.114 |

Comp. Example 2

|  | R20 | R19 | R18 | R17 | R16 | R15 | R14 |
|---|---|---|---|---|---|---|---|
| L20 | 2.49 | 0.304 | 2.908 | 2.8085 | 3.0383 | 2.3831 | 3.0539 |
| L19 | 2.767 | 1.248 | 3.127 | 3.0895 | 2.6173 | 1.7906 | 1.1591 |
| L18 | 2.56 | 2.552 | 3.08 | 3.2032 | 3.3938 | 1.953 | 2.3059 |
| L17 | 1.904 | 1.858 | 1.982 | 2.3249 | 2.6396 | 2.6013 | 2.9211 |
| L16 | 1.301 | 1.61 | 1.24 | 1.0794 | 3.2855 | 2.4741 | 3.0815 |
| L15 | 1.541 | 1.898 | 0.991 | 1.3884 | 2.7469 | 3.0295 | 2.3119 |
| L14 | 2.382 | 2.174 | 2.388 | 2.3374 | 2.7348 | 1.9998 | 1.0779 |

[Fig. 5A]
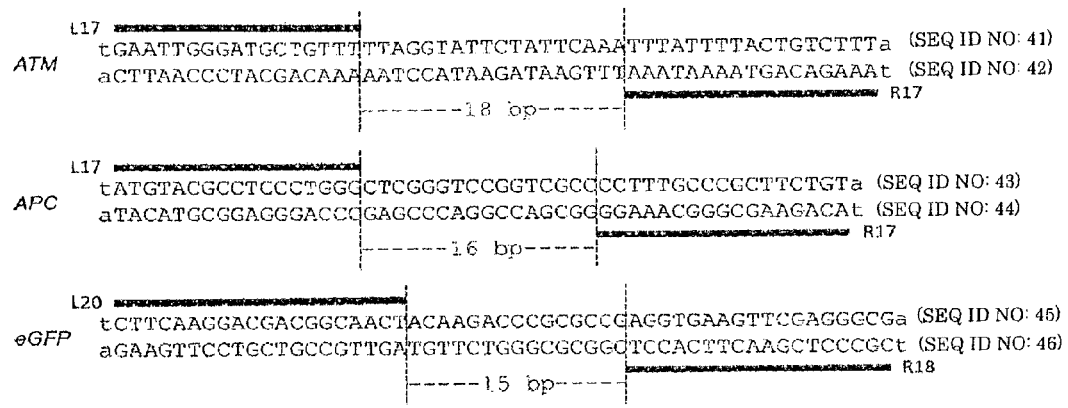
[Fig. 5B]
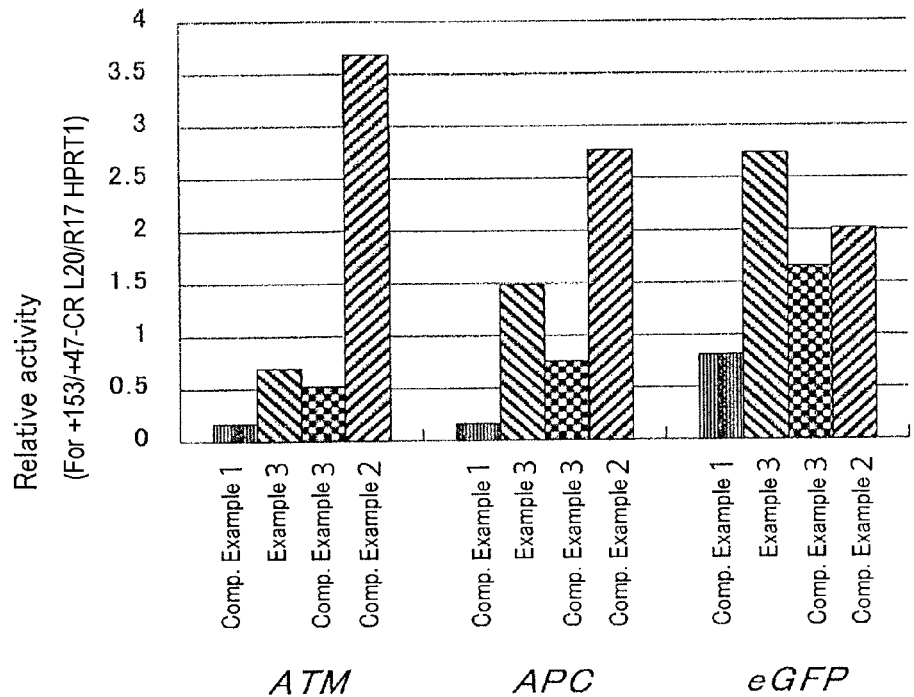

[Fig. 6A]

- Original sequence (no mismatches)

```
L19 ━━━━━━━━━━━━━━━━━━━━━
    tCCATTCCTATGACTGTAGATTTTATCAGACTGAAGAGCTATTGTGTGAGTATa (SEQ ID NO: 47)
    aGGTAAGGATACTGACATCTAAAATAGTCTGACTTCTCGATAACACACTCATAt (SEQ ID NO: 48)
                        |----15 bp----|━━━━━━━━━━━━━━━━━ R18
```

- L: 1 mismatch / R: 0 mismatch

```
    tCCATTCCgATGACTGTAGATTTTATCAGACTGAAGAGCTATTGTGTGAGTATa (SEQ ID NO: 49)
    aGGTAAGGcTACTGACATCTAAAATAGTCTGACTTCTCGATAACACACTCATAt (SEQ ID NO: 50)
```

- L: 1 mismatch / R: 1 mismatch

```
    tCCATTCCgATGACTGTAGATTTTATCAGACTGAAGAGCTATTGaGTGAGTATa (SEQ ID NO: 51)
    aGGTAAGGcTACTGACATCTAAAATAGTCTGACTTCTCGATAACtCACTCATAt (SEQ ID NO: 52)
```

- L: 2 mismatches / R: 2 mismatches

```
    tCtATTCCgATGACTGTAGATTTTATCAGACTGAAGAGCTATTGaGTGAcTATa (SEQ ID NO: 53)
    aGaTAAGGcTACTGACATCTAAAATAGTCTGACTTCTCGATAACtCACTgATAt (SEQ ID NO: 54)
```

[Fig. 6B]

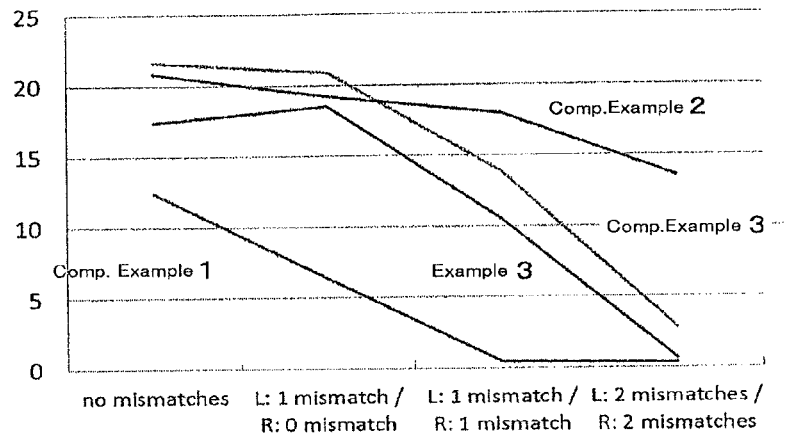

```
                         SEQUENCE LISTING

<160> NUMBER OF SEQ ID NOS: 54

<210> SEQ ID NO 1
    <211> LENGTH: 102
    <212> TYPE: DNA
    <213> ORGANISM: Homo sapiens
    <220> FEATURE:
    <221> NAME/KEY: CDS
    <222> LOCATION: (1)..(102)

<400> SEQUENCE: 1 ctg acc ccg gac cag gtg gtt gca atc gcg tca cac gat ggg gga aag       48
    Leu Thr Pro Asp Gln Val Val Ala Ile Ala Ser His Asp Gly Gly Lys
    1               5                   10                  15 cag gcc cta gaa acc gtt cag cga ctc ctg ccc gtc ctg tgc cag gac       96
    Gln Ala Leu Glu Thr Val Gln Arg Leu Leu Pro Val Leu Cys Gln Asp
                    20                  25                  30 cac ggc                                                              102
    His Gly <210> SEQ ID NO 2
    <211> LENGTH: 34
    <212> TYPE: PRT
    <213> ORGANISM: Homo sapiens

<400> SEQUENCE: 2

Leu Thr Pro Asp Gln Val Val Ala Ile Ala Ser His Asp Gly Gly Lys
    1               5                   10                  15

Gln Ala Leu Glu Thr Val Gln Arg Leu Leu Pro Val Leu Cys Gln Asp
                    20                  25                  30

His Gly

<210> SEQ ID NO 3
    <211> LENGTH: 102
    <212> TYPE: DNA
    <213> ORGANISM: Homo sapiens
    <220> FEATURE:
    <221> NAME/KEY: CDS
    <222> LOCATION: (1)..(102)

<400> SEQUENCE: 3 ctg acc ccc gac cag gtt gtc gct att gct agt aac ggc gga ggc aaa       48
    Leu Thr Pro Asp Gln Val Val Ala Ile Ala Ser Asn Gly Gly Gly Lys
    1               5                   10                  15 cag gcg ctg gaa aca gtt cag cgc ctc ttg ccg gtc ttg tgt cag gac       96
    Gln Ala Leu Glu Thr Val Gln Arg Leu Leu Pro Val Leu Cys Gln Asp
                    20                  25                  30
```

```
cac ggc                                                           102
His Gly <210> SEQ ID NO 4
<211> LENGTH: 34
<212> TYPE: PRT
<213> ORGANISM: Homo sapiens

<400> SEQUENCE: 4

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 5
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 5 ctg acc cca gac cag gtt gtg gcc atc gcc agc aac ata ggt ggc aag    48
Leu Thr Pro Asp Gln Val Val Ala Ile Ala Ser Asn Ile Gly Gly Lys
1               5                   10                  15 cag gcc ctc gaa acc gtc cag aga ctg tta ccg gtt ctc tgc cag gac    96
Gln Ala Leu Glu Thr Val Gln Arg Leu Leu Pro Val Leu Cys Gln Asp
            20                  25                  30 cac ggc                                                           102
His Gly

<210> SEQ ID NO 6
<211> LENGTH: 34
<212> TYPE: PRT
<213> ORGANISM: Homo sapiens

<400> SEQUENCE: 6

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 7
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 7 ctg acc cca gac caa gtt gtc gcg att gca agc aac aac gga ggc aaa    48
Leu Thr Pro Asp Gln Val Val Ala Ile Ala Ser Asn Asn Gly Gly Lys
1               5                   10                  15 caa gcc tta gaa aca gtc cag aga ttg ttg ccg gtg ctg tgc caa gac    96
Gln Ala Leu Glu Thr Val Gln Arg Leu Leu Pro Val Leu Cys Gln Asp
            20                  25                  30 cac ggc                                                           102
His Gly
```

<210> SEQ ID NO 8
<211> LENGTH: 34
<212> TYPE: PRT
<213> ORGANISM: Homo sapiens

<400> SEQUENCE: 8

Leu Thr Pro Asp Gln Val Val Ala Ile Ala Ser Asn Asn Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 9
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 9 ctg acc ccg gaa cag gtg gtt gca atc gcg tca cac gat ggg gga aag      48
Leu Thr Pro Glu Gln Val Val Ala Ile Ala Ser His Asp Gly Gly Lys
1               5                   10                  15 cag gcc cta gaa acc gtt cag cga ctc ctg ccc gtc ctg tgc cag gcc      96
Gln Ala Leu Glu Thr Val Gln Arg Leu Leu Pro Val Leu Cys Gln Ala
            20                  25                  30 cac ggc                                                             102
His Gly

<210> SEQ ID NO 10
<211> LENGTH: 34
<212> TYPE: PRT
<213> ORGANISM: Homo sapiens

<400> SEQUENCE: 10

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 11
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 11 ctg acc ccc gaa cag gtt gtc gct att gct agt aac ggc gga ggc aaa      48
Leu Thr Pro Glu Gln Val Val Ala Ile Ala Ser Asn Gly Gly Gly Lys
1               5                   10                  15 cag gcg ctg gaa aca gtt cag cgc ctc ttg ccg gtc ttg tgt cag gcc      96
Gln Ala Leu Glu Thr Val Gln Arg Leu Leu Pro Val Leu Cys Gln Ala
            20                  25                  30 cac ggc                                                             102
His Gly

<210> SEQ ID NO 12

```
<211> LENGTH: 34
<212> TYPE: PRT
<213> ORGANISM: Homo sapiens

<400> SEQUENCE: 12

Leu Thr Pro Glu Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 13
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 13 ctg acc cca gaa cag gtt gtg gcc atc gcc agc aac ata ggt ggc aag      48
Leu Thr Pro Glu Gln Val Val Ala Ile Ala Ser Asn Ile Gly Gly Lys
1               5                   10                  15 cag gcc ctc gaa acc gtc cag aga ctg tta ccg gtt ctc tgc cag gcc      96
Gln Ala Leu Glu Thr Val Gln Arg Leu Leu Pro Val Leu Cys Gln Ala
            20                  25                  30 cac ggc                                                             102
His Gly

<210> SEQ ID NO 14
<211> LENGTH: 34
<212> TYPE: PRT
<213> ORGANISM: Homo sapiens

<400> SEQUENCE: 14

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 15
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 15 ctg acc cca gaa caa gtt gtc gcg att gca agc aac aac gga ggc aaa      48
Leu Thr Pro Glu Gln Val Val Ala Ile Ala Ser Asn Asn Gly Gly Lys
1               5                   10                  15 caa gcc tta gaa aca gtc cag aga ttg ttg ccg gtg ctg tgc caa gcc      96
Gln Ala Leu Glu Thr Val Gln Arg Leu Leu Pro Val Leu Cys Gln Ala
            20                  25                  30 cac ggc                                                             102
His Gly

<210> SEQ ID NO 16
<211> LENGTH: 34
<212> TYPE: PRT
<213> ORGANISM: Homo sapiens
```

<400> SEQUENCE: 16

Leu Thr Pro Glu Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 17
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 17 ctg acc ccg gac cag gtg gtt gca atc gcg tca cac gat ggg gga aag      48
Leu Thr Pro Asp Gln Val Val Ala Ile Ala Ser His Asp Gly Gly Lys
1               5                   10                  15 cag gcc cta gaa acc gtt cag cga ctc ctg ccc gtc ctg tgc cag gcc      96
Gln Ala Leu Glu Thr Val Gln Arg Leu Leu Pro Val Leu Cys Gln Ala
            20                  25                  30 cac ggc                                                             102
His Gly

<210> SEQ ID NO 18
<211> LENGTH: 34
<212> TYPE: PRT
<213> ORGANISM: Homo sapiens

<400> SEQUENCE: 18

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 19
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 19 ctg acc ccc gac cag gtt gtc gct att gct agt aac ggc gga ggc aaa      48
Leu Thr Pro Asp Gln Val Val Ala Ile Ala Ser Asn Gly Gly Gly Lys
1               5                   10                  15 cag gcg ctg gaa aca gtt cag cgc ctc ttg ccg gtc ttg tgt cag gcc      96
Gln Ala Leu Glu Thr Val Gln Arg Leu Leu Pro Val Leu Cys Gln Ala
            20                  25                  30 cac ggc                                                             102
His Gly

<210> SEQ ID NO 20
<211> LENGTH: 34
<212> TYPE: PRT
<213> ORGANISM: Homo sapiens

<400> SEQUENCE: 20

-continued

```
Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 21
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 21 ctg acc cca gac cag gtt gtg gcc atc gcc agc aac ata ggt ggc aag      48
Leu Thr Pro Asp Gln Val Val Ala Ile Ala Ser Asn Ile Gly Gly Lys
1               5                   10                  15 cag gcc ctc gaa acc gtc cag aga ctg tta ccg gtt ctc tgc cag gcc      96
Gln Ala Leu Glu Thr Val Gln Arg Leu Leu Pro Val Leu Cys Gln Ala
            20                  25                  30 cac ggc                                                             102
His Gly

<210> SEQ ID NO 22
<211> LENGTH: 34
<212> TYPE: PRT
<213> ORGANISM: Homo sapiens

<400> SEQUENCE: 22

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 23
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 23 ctg acc cca gac caa gtt gtc gcg att gca agc aac aac gga ggc aaa      48
Leu Thr Pro Asp Gln Val Val Ala Ile Ala Ser Asn Asn Gly Gly Lys
1               5                   10                  15 caa gcc tta gaa aca gtc cag aga ttg ttg cct gtg ctg tgc caa gcc      96
Gln Ala Leu Glu Thr Val Gln Arg Leu Leu Pro Val Leu Cys Gln Ala
            20                  25                  30 cac ggc                                                             102
His Gly

<210> SEQ ID NO 24
<211> LENGTH: 34
<212> TYPE: PRT
<213> ORGANISM: Homo sapiens

<400> SEQUENCE: 24

Leu Thr Pro Asp Gln Val Val Ala Ile Ala Ser Asn Asn Gly Gly Lys
1               5                   10                  15
```

Gln Ala Leu Glu Thr Val Gln Arg Leu Pro Val Leu Cys Gln Ala
            20                  25                  30

His Gly

<210> SEQ ID NO 25
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 25 ctg acc ccg gcc cag gtg gtt gca atc gcg tca cac gat ggg gga aag      48
Leu Thr Pro Ala Gln Val Val Ala Ile Ala Ser His Asp Gly Gly Lys
1               5                   10                  15 cag gcc cta gaa acc gtt cag cga ctc ctg ccc gtc ctg tgc cag gac      96
Gln Ala Leu Glu Thr Val Gln Arg Leu Leu Pro Val Leu Cys Gln Asp
            20                  25                  30 cac ggc                                                              102
His Gly <210> SEQ ID NO 26
<211> LENGTH: 34
<212> TYPE: PRT
<213> ORGANISM: Homo sapiens

<400> SEQUENCE: 26

Leu Thr Pro Ala Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 27
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 27 ctg acc ccc gcc cag gtt gtc gct att gct agt aac ggc gga ggc aaa      48
Leu Thr Pro Ala Gln Val Val Ala Ile Ala Ser Asn Gly Gly Gly Lys
1               5                   10                  15 cag gcg ctg gaa aca gtt cag cgc ctc ttg ccg gtc ttg tgt cag gac      96
Gln Ala Leu Glu Thr Val Gln Arg Leu Leu Pro Val Leu Cys Gln Asp
            20                  25                  30 cac ggc                                                              102
His Gly <210> SEQ ID NO 28
<211> LENGTH: 34
<212> TYPE: PRT
<213> ORGANISM: Homo sapiens

<400> SEQUENCE: 28

Leu Thr Pro Ala Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 29
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 29

```
ctg acc cca gcc cag gtt gtg gcc atc gcc agc aac ata ggt ggc aag    48
Leu Thr Pro Ala Gln Val Val Ala Ile Ala Ser Asn Ile Gly Gly Lys
1               5                   10                  15 cag gcc ctc gaa acc gtc cag aga ctg tta ccg gtt ctc tgc cag gac    96
Gln Ala Leu Glu Thr Val Gln Arg Leu Leu Pro Val Leu Cys Gln Asp
            20                  25                  30 cac ggc                                                           102
His Gly
```

<210> SEQ ID NO 30
<211> LENGTH: 34
<212> TYPE: PRT
<213> ORGANISM: Homo sapiens

<400> SEQUENCE: 30

```
Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly
```

<210> SEQ ID NO 31
<211> LENGTH: 102
<212> TYPE: DNA
<213> ORGANISM: Homo sapiens
<220> FEATURE:
<221> NAME/KEY: CDS
<222> LOCATION: (1)..(102)

<400> SEQUENCE: 31

```
ctg acc cca gcc caa gtt gtc gcg att gca agc aac aac gga ggc aaa    48
Leu Thr Pro Ala Gln Val Val Ala Ile Ala Ser Asn Asn Gly Gly Lys
1               5                   10                  15 caa gcc tta gaa aca gtc cag aga ttg ttg ccg gtg ctg tgc caa gac    96
Gln Ala Leu Glu Thr Val Gln Arg Leu Leu Pro Val Leu Cys Gln Asp
            20                  25                  30 cac ggc                                                           102
His Gly
```

<210> SEQ ID NO 32
<211> LENGTH: 34
<212> TYPE: PRT
<213> ORGANISM: Homo sapiens

<400> SEQUENCE: 32

```
Leu Thr Pro Ala Gln Val Val Ala Ile Ala Ser Asn Asn Gly Gly Lys
1               5                   10                  15

Gln Ala Leu Glu Thr Val Gln Arg Leu Leu Pro Val Leu Cys Gln Asp
            20                  25                  30

His Gly
```

<210> SEQ ID NO 33
<211> LENGTH: 2997
<212> TYPE: DNA
<213> ORGANISM: Homo sapiens
<220> FEATURE:
<221> NAME/KEY: CDS
<222> LOCATION: (1)..(2997)

<400> SEQUENCE: 33

```
atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
                20                  25                  30 aga atg cat gcg gcc ccg cga cgg cgt gct gcg caa ccc tcc gac gct     144
Arg Met His Ala Ala Pro Arg Arg Arg Ala Ala Gln Pro Ser Asp Ala
            35                  40                  45 tcg ccg gcc gcg cag gtg gat cta cgc acg ctc ggc tac agt cag cag     192
Ser Pro Ala Ala Gln Val Asp Leu Arg Thr Leu Gly Tyr Ser Gln Gln
        50                  55                  60 cag caa gag aag atc aaa ccg aag gtg cgt tcg aca gtg gcg cag cac     240
Gln Gln Glu Lys Ile Lys Pro Lys Val Arg Ser Thr Val Ala Gln His
65                  70                  75                  80 cac gag gca ctg gtg ggc cat ggg ttt aca cac gcg cac atc gtt gcg     288
His Glu Ala Leu Val Gly His Gly Phe Thr His Ala His Ile Val Ala
                85                  90                  95 ctc agc caa cac ccg gca gcg tta ggg acc gtc gct gtc acg tat cag     336
Leu Ser Gln His Pro Ala Ala Leu Gly Thr Val Ala Val Thr Tyr Gln
                100                 105                 110 cac ata atc acg gcg ttg cca gag gcg aca cac gaa gac atc gtt ggc     384
His Ile Ile Thr Ala Leu Pro Glu Ala Thr His Glu Asp Ile Val Gly
            115                 120                 125 gtc ggc aaa cag tgg tcc ggc gca cgc gcc ctg gag gcc ttg ctc acg     432
Val Gly Lys Gln Trp Ser Gly Ala Arg Ala Leu Glu Ala Leu Leu Thr
        130                 135                 140 gat gcg ggg gag ttg aga ggt ccg ccg tta cag ttg gac aca ggc caa     480
Asp Ala Gly Glu Leu Arg Gly Pro Pro Leu Gln Leu Asp Thr Gly Gln
145                 150                 155                 160 ctt gtg aag att gca aaa cgt ggc ggc gtg acc gca atg gag gca gtg     528
Leu Val Lys Ile Ala Lys Arg Gly Gly Val Thr Ala Met Glu Ala Val
                165                 170                 175 cat gca tcg cgc aat gcg ctc acg gga gca ccc ctc aac ctg acc cca     576
His Ala Ser Arg Asn Ala Leu Thr Gly Ala Pro Leu Asn Leu Thr Pro
                180                 185                 190 gac cag gtt gtg gcc atc gcc agc aac ata ggt ggc aag cag gcc ctc     624
Asp Gln Val Val Ala Ile Ala Ser Asn Ile Gly Gly Lys Gln Ala Leu
            195                 200                 205 gaa acc gtc cag aga ctg tta ccg gtt ctc tgc cag gac cac ggc ctg     672
Glu Thr Val Gln Arg Leu Leu Pro Val Leu Cys Gln Asp His Gly Leu
        210                 215                 220 acc ccc gaa cag gtt gtc gct att gct agt aac ggc gga ggc aaa cag     720
Thr Pro Glu Gln Val Val Ala Ile Ala Ser Asn Gly Gly Gly Lys Gln
225                 230                 235                 240 gcg ctg gaa aca gtt cag cgc ctc ttg ccg gtc ttg tgt cag gcc cac     768
Ala Leu Glu Thr Val Gln Arg Leu Leu Pro Val Leu Cys Gln Ala His
                245                 250                 255 ggc ctg acc cca gac cag gtt gtg gcc atc gcc agc aac ata ggt ggc     816
Gly Leu Thr Pro Asp Gln Val Val Ala Ile Ala Ser Asn Ile Gly Gly
                260                 265                 270 aag cag gcc ctc gaa acc gtc cag aga ctg tta ccg gtt ctc tgc cag     864
Lys Gln Ala Leu Glu Thr Val Gln Arg Leu Leu Pro Val Leu Cys Gln
```

```
Lys Gln Ala Leu Glu Thr Val Gln Arg Leu Leu Pro Val Leu Cys Gln
            275                 280                 285 gcc cac ggc ctg acc ccg gcc cag gtg gtt gca atc gcg tca cac gat      912
Ala His Gly Leu Thr Pro Ala Gln Val Val Ala Ile Ala Ser His Asp
290                 295                 300 ggg gga aag cag gcc cta gaa acc gtt cag cga ctc ctg ccc gtc ctg      960
Gly Gly Lys Gln Ala Leu Glu Thr Val Gln Arg Leu Leu Pro Val Leu
305                 310                 315                 320 tgc cag gac cac ggc ctg acc ccc gac cag gtt gtc gct att gct agt     1008
Cys Gln Asp His Gly Leu Thr Pro Asp Gln Val Val Ala Ile Ala Ser
                325                 330                 335 aac ggc gga ggc aaa cag gcg ctg gaa aca gtt cag cgc ctc ttg ccg     1056
Asn Gly Gly Gly Lys Gln Ala Leu Glu Thr Val Gln Arg Leu Leu Pro
            340                 345                 350 gtc ttg tgt cag gac cac ggc ctg acc ccg gaa cag gtg gtt gca atc     1104
Val Leu Cys Gln Asp His Gly Leu Thr Pro Glu Gln Val Val Ala Ile
        355                 360                 365 gcg tca cac gat ggg gga aag cag gcc cta gaa acc gtt cag cga ctc     1152
Ala Ser His Asp Gly Gly Lys Gln Ala Leu Glu Thr Val Gln Arg Leu
370                 375                 380 ctg ccc gtc ctg tgc cag gcc cac ggc ctg acc cca gac cag gtt gtg     1200
Leu Pro Val Leu Cys Gln Ala His Gly Leu Thr Pro Asp Gln Val Val
385                 390                 395                 400 gcc atc gcc agc aac ata ggt ggc aag cag gcc ctc gaa acc gtc cag     1248
Ala Ile Ala Ser Asn Ile Gly Gly Lys Gln Ala Leu Glu Thr Val Gln
                405                 410                 415 aga ctg tta ccg gtt ctc tgc cag gcc cac ggc ctg acc ccg gcc cag     1296
Arg Leu Leu Pro Val Leu Cys Gln Ala His Gly Leu Thr Pro Ala Gln
            420                 425                 430 gtg gtt gca atc gcg tca cac gat ggg gga aag cag gcc cta gaa acc     1344
Val Val Ala Ile Ala Ser His Asp Gly Gly Lys Gln Ala Leu Glu Thr
        435                 440                 445 gtt cag cga ctc ctg ccc gtc ctg tgc cag gac cac ggc ctg acc cca     1392
Val Gln Arg Leu Leu Pro Val Leu Cys Gln Asp His Gly Leu Thr Pro
450                 455                 460 gac cag gtt gtg gcc atc gcc agc aac ata ggt ggc aag cag gcc ctc     1440
Asp Gln Val Val Ala Ile Ala Ser Asn Ile Gly Gly Lys Gln Ala Leu
465                 470                 475                 480 gaa acc gtc cag aga ctg tta ccg gtt ctc tgc cag gac cac ggc ctg     1488
Glu Thr Val Gln Arg Leu Leu Pro Val Leu Cys Gln Asp His Gly Leu
                485                 490                 495 acc ccg gaa cag gtg gtt gca atc gcg tca cac gat ggg gga aag cag     1536
Thr Pro Glu Gln Val Val Ala Ile Ala Ser His Asp Gly Gly Lys Gln
            500                 505                 510 gcc cta gaa acc gtt cag cga ctc ctg ccc gtc ctg tgc cag gcc cac     1584
Ala Leu Glu Thr Val Gln Arg Leu Leu Pro Val Leu Cys Gln Ala His
        515                 520                 525 ggc ctg acc cca gac cag gtt gtg gcc atc gcc agc aac ata ggt ggc     1632
Gly Leu Thr Pro Asp Gln Val Val Ala Ile Ala Ser Asn Ile Gly Gly
530                 535                 540 aag cag gcc ctc gaa acc gtc cag aga ctg tta ccg gtt ctc tgc cag     1680
Lys Gln Ala Leu Glu Thr Val Gln Arg Leu Leu Pro Val Leu Cys Gln
545                 550                 555                 560 gcc cac ggc ctg acc cca gcc cag gtt gtg gcc atc gcc agc aac ata     1728
Ala His Gly Leu Thr Pro Ala Gln Val Val Ala Ile Ala Ser Asn Ile
                565                 570                 575 ggt ggc aag cag gcc ctc gaa acc gtc cag aga ctg tta ccg gtt ctc     1776
Gly Gly Lys Gln Ala Leu Glu Thr Val Gln Arg Leu Leu Pro Val Leu
            580                 585                 590
```

```
                                                                            -continued tgc cag gac cac ggc ctg acc ccc gac cag gtt gtc gct att gct agt          1824
Cys Gln Asp His Gly Leu Thr Pro Asp Gln Val Val Ala Ile Ala Ser
        595                 600                 605 aac ggc gga ggc aaa cag gcg ctg gaa aca gtt cag cgc ctc ttg ccg          1872
Asn Gly Gly Gly Lys Gln Ala Leu Glu Thr Val Gln Arg Leu Leu Pro
610                 615                 620 gtc ttg tgt cag gac cac ggc ctg acc cca gaa cag gtt gtg gcc atc          1920
Val Leu Cys Gln Asp His Gly Leu Thr Pro Glu Gln Val Val Ala Ile
625                 630                 635                 640 gcc agc aac ata ggt ggc aag cag gcc ctc gaa acc gtc cag aga ctg          1968
Ala Ser Asn Ile Gly Gly Lys Gln Ala Leu Glu Thr Val Gln Arg Leu
                645                 650                 655 tta ccg gtt ctc tgc cag gcc cac ggc ctg acc cca gac caa gtt gtc          2016
Leu Pro Val Leu Cys Gln Ala His Gly Leu Thr Pro Asp Gln Val Val
            660                 665                 670 gcg att gca agc aac aac gga ggc aaa caa gcc tta gaa aca gtc cag          2064
Ala Ile Ala Ser Asn Asn Gly Gly Lys Gln Ala Leu Glu Thr Val Gln
        675                 680                 685 aga ttg ttg ccg gtg ctg tgc caa gcc cac ggc ctg acc ccg gcc cag          2112
Arg Leu Leu Pro Val Leu Cys Gln Ala His Gly Leu Thr Pro Ala Gln
690                 695                 700 gtg gtt gca atc gcg tca cac gat ggg gga aag cag gcc cta gaa acc          2160
Val Val Ala Ile Ala Ser His Asp Gly Gly Lys Gln Ala Leu Glu Thr
705                 710                 715                 720 gtt cag cga ctc ctg ccc gtc ctg tgc cag gac cac ggc ctg acg cct          2208
Val Gln Arg Leu Leu Pro Val Leu Cys Gln Asp His Gly Leu Thr Pro
                725                 730                 735 gag cag gta gtg gct att gca tcc aac gga ggg ggc aga ccc gca ctg          2256
Glu Gln Val Val Ala Ile Ala Ser Asn Gly Gly Gly Arg Pro Ala Leu
            740                 745                 750 gag tca atc gtg gcc cag ctt tcg agg ccg gac ccc gcg ctg gcc gca          2304
Glu Ser Ile Val Ala Gln Leu Ser Arg Pro Asp Pro Ala Leu Ala Ala
        755                 760                 765 ctc act aat gat cat ctt gta gcg ctg gcc tgc ctc ggc gga cgt cct          2352
Leu Thr Asn Asp His Leu Val Ala Leu Ala Cys Leu Gly Gly Arg Pro
770                 775                 780 gcc atg gat gca gtg aaa aag gga ttg ccg cac gcg ccg gaa ttg atc          2400
Ala Met Asp Ala Val Lys Lys Gly Leu Pro His Ala Pro Glu Leu Ile
785                 790                 795                 800 aga tcc cag cta gtg aaa tct gaa ttg gaa gag aag aaa tct gaa ctt          2448
Arg Ser Gln Leu Val Lys Ser Glu Leu Glu Glu Lys Lys Ser Glu Leu
                805                 810                 815 aga cat aaa ttg aaa tat gtg cca cat gaa tat att gaa ttg att gaa          2496
Arg His Lys Leu Lys Tyr Val Pro His Glu Tyr Ile Glu Leu Ile Glu
            820                 825                 830 atc gca aga aat tca act cag gat aga atc ctt gaa atg aag gtg atg          2544
Ile Ala Arg Asn Ser Thr Gln Asp Arg Ile Leu Glu Met Lys Val Met
        835                 840                 845 gag ttc ttt atg aag gtt tat ggt tat cgt ggt aaa cat ttg ggt gga          2592
Glu Phe Phe Met Lys Val Tyr Gly Tyr Arg Gly Lys His Leu Gly Gly
850                 855                 860 tca agg aaa cca gac gga gca att tat act gtc gga tct cct att gat          2640
Ser Arg Lys Pro Asp Gly Ala Ile Tyr Thr Val Gly Ser Pro Ile Asp
865                 870                 875                 880 tac ggt gtg atc gtt gat act aag gca tat tca gga ggt tat aat ctt          2688
Tyr Gly Val Ile Val Asp Thr Lys Ala Tyr Ser Gly Gly Tyr Asn Leu
                885                 890                 895 cca att ggt caa gca gat gaa atg caa aga tat gtc gaa gag aat caa          2736
Pro Ile Gly Gln Ala Asp Glu Met Gln Arg Tyr Val Glu Glu Asn Gln
            900                 905                 910
```

-continued

| | | |
|---|---|---|
| aca aga aac aag cat atc aac cct aat gaa tgg tgg aaa gtc tat cca<br>Thr Arg Asn Lys His Ile Asn Pro Asn Glu Trp Trp Lys Val Tyr Pro<br>        915                    920                    925 | | 2784 |
| tct tca gta aca gaa ttt aag ttc ttg ttt gtg agt ggt cat ttc aaa<br>Ser Ser Val Thr Glu Phe Lys Phe Leu Phe Val Ser Gly His Phe Lys<br>        930                    935                    940 | | 2832 |
| gga aac tac aaa gct cag ctt aca aga ttg aat cat atc act aat tgt<br>Gly Asn Tyr Lys Ala Gln Leu Thr Arg Leu Asn His Ile Thr Asn Cys<br>945                    950                    955                    960 | | 2880 |
| aat gga gct gtt ctt agt gta gaa gag ctt ttg att ggt gga gaa atg<br>Asn Gly Ala Val Leu Ser Val Glu Glu Leu Leu Ile Gly Gly Glu Met<br>                  965                    970                    975 | | 2928 |
| att aaa gct ggt aca ttg aca ctt gag gaa gtg aga agg aaa ttt aat<br>Ile Lys Ala Gly Thr Leu Thr Leu Glu Glu Val Arg Arg Lys Phe Asn<br>        980                    985                    990 | | 2976 |
| aac ggt gag ata aac ttt taa<br>Asn Gly Glu Ile Asn Phe<br>        995 | | 2997 |

<210> SEQ ID NO 34
<211> LENGTH: 998
<212> TYPE: PRT
<213> ORGANISM: Homo sapiens

<400> SEQUENCE: 34

Met Ala Ser Ser Pro Pro Lys Lys Lys Arg Lys Val Ala Ala Asp
1               5                   10                  15

Tyr Lys Asp Asp Asp Lys Ser Trp Lys Asp Ala Ser Gly Trp Ser
            20                  25                  30

Arg Met His Ala Ala Pro Arg Arg Ala Gln Pro Ser Asp Ala
        35                  40                  45

Ser Pro Ala Ala Gln Val Asp Leu Arg Thr Leu Gly Tyr Ser Gln Gln
50                  55                  60

Gln Gln Glu Lys Ile Lys Pro Lys Val Arg Ser Thr Val Ala Gln His
65                  70                  75                  80

His Glu Ala Leu Val Gly His Gly Phe Thr His Ala His Ile Val Ala
                85                  90                  95

Leu Ser Gln His Pro Ala Ala Leu Gly Thr Val Ala Val Thr Tyr Gln
            100                 105                 110

His Ile Ile Thr Ala Leu Pro Glu Ala Thr His Glu Asp Ile Val Gly
        115                 120                 125

Val Gly Lys Gln Trp Ser Gly Ala Arg Ala Leu Glu Ala Leu Leu Thr
    130                 135                 140

Asp Ala Gly Glu Leu Arg Gly Pro Pro Leu Gln Leu Asp Thr Gly Gln
145                 150                 155                 160

Leu Val Lys Ile Ala Lys Arg Gly Gly Val Thr Ala Met Glu Ala Val
                165                 170                 175

His Ala Ser Arg Asn Ala Leu Thr Gly Ala Pro Leu Asn Leu Thr Pro
            180                 185                 190

Asp Gln Val Val Ala Ile Ala Ser Asn Ile Gly Gly Lys Gln Ala Leu
        195                 200                 205

Glu Thr Val Gln Arg Leu Leu Pro Val Leu Cys Gln Asp His Gly Leu
    210                 215                 220

Thr Pro Glu Gln Val Val Ala Ile Ala Ser Asn Gly Gly Gly Lys Gln
225                 230                 235                 240

Ala Leu Glu Thr Val Gln Arg Leu Leu Pro Val Leu Cys Gln Ala His

```
                    245                 250                 255
Gly Leu Thr Pro Asp Gln Val Ala Ile Ala Ser Asn Ile Gly Gly
            260                 265                 270

Lys Gln Ala Leu Glu Thr Val Gln Arg Leu Leu Pro Val Leu Cys Gln
275                 280                 285

Ala His Gly Leu Thr Pro Ala Gln Val Val Ala Ile Ala Ser His Asp
        290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
                325                 330                 335

Asn Gly Gly Lys Gln Ala Leu Glu Thr Val Gln Arg Leu Leu Pro
            340                 345                 350

Val Leu Cys Gln Asp His Gly Leu Thr Pro Glu Gln Val Val Ala Ile
            355                 360                 365

Ala Ser His Asp Gly Gly Lys Gln Ala Leu Glu Thr Val Gln Arg Leu
        370                 375                 380

Leu Pro Val Leu Cys Gln Ala His Gly Leu Thr Pro Asp Gln Val Val
385                 390                 395                 400

Ala Ile Ala Ser Asn Ile Gly Gly Lys Gln Ala Leu Glu Thr Val Gln
                405                 410                 415

Arg Leu Leu Pro Val Leu Cys Gln Ala His Gly Leu Thr Pro Ala Gln
            420                 425                 430

Val Val Ala Ile Ala Ser His Asp Gly Gly Lys Gln Ala Leu Glu Thr
        435                 440                 445

Val Gln Arg Leu Leu Pro Val Leu Cys Gln Asp His Gly Leu Thr Pro
    450                 455                 460

Asp Gln Val Val Ala Ile Ala Ser Asn Ile Gly Gly Lys Gln Ala Leu
465                 470                 475                 480

Glu Thr Val Gln Arg Leu Leu Pro Val Leu Cys Gln Asp His Gly Leu
                485                 490                 495

Thr Pro Glu Gln Val Val Ala Ile Ala Ser His Asp Gly Gly Lys Gln
            500                 505                 510

Ala Leu Glu Thr Val Gln Arg Leu Leu Pro Val Leu Cys Gln Ala His
        515                 520                 525

Gly Leu Thr Pro Asp Gln Val Ala Ile Ala Ser Asn Ile Gly Gly
    530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser Asn Ile
                565                 570                 575

Gly Gly Lys Gln Ala Leu Glu Thr Val Gln Arg Leu Leu Pro Val Leu
            580                 585                 590

Cys Gln Asp His Gly Leu Thr Pro Asp Gln Val Val Ala Ile Ala Ser
        595                 600                 605

Asn Gly Gly Lys Gln Ala Leu Glu Thr Val Gln Arg Leu Leu Pro
    610                 615                 620

Val Leu Cys Gln Asp His Gly Leu Thr Pro Glu Gln Val Val Ala Ile
625                 630                 635                 640

Ala Ser Asn Ile Gly Gly Lys Gln Ala Leu Glu Thr Val Gln Arg Leu
                645                 650                 655

Leu Pro Val Leu Cys Gln Ala His Gly Leu Thr Pro Asp Gln Val Val
            660                 665                 670
```

-continued

```
Ala Ile Ala Ser Asn Asn Gly Gly Lys Gln Ala Leu Glu Thr Val Gln
            675                 680                 685

Arg Leu Leu Pro Val Leu Cys Gln Ala His Gly Leu Thr Pro Ala Gln
        690                 695                 700

Val Val Ala Ile Ala Ser His Asp Gly Gly Lys Gln Ala Leu Glu Thr
705                 710                 715                 720

Val Gln Arg Leu Leu Pro Val Leu Cys Gln Asp His Gly Leu Thr Pro
                725                 730                 735

Glu Gln Val Val Ala Ile Ala Ser Asn Gly Gly Gly Arg Pro Ala Leu
            740                 745                 750

Glu Ser Ile Val Ala Gln Leu Ser Arg Pro Asp Pro Ala Leu Ala Ala
            755                 760                 765

Leu Thr Asn Asp His Leu Val Ala Leu Ala Cys Leu Gly Gly Arg Pro
        770                 775                 780

Ala Met Asp Ala Val Lys Lys Gly Leu Pro His Ala Pro Glu Leu Ile
785                 790                 795                 800

Arg Ser Gln Leu Val Lys Ser Glu Leu Glu Glu Lys Lys Ser Glu Leu
                805                 810                 815

Arg His Lys Leu Lys Tyr Val Pro His Glu Tyr Ile Glu Leu Ile Glu
            820                 825                 830

Ile Ala Arg Asn Ser Thr Gln Asp Arg Ile Leu Glu Met Lys Val Met
        835                 840                 845

Glu Phe Phe Met Lys Val Tyr Gly Tyr Arg Gly Lys His Leu Gly Gly
850                 855                 860

Ser Arg Lys Pro Asp Gly Ala Ile Tyr Thr Val Gly Ser Pro Ile Asp
865                 870                 875                 880

Tyr Gly Val Ile Val Asp Thr Lys Ala Tyr Ser Gly Gly Tyr Asn Leu
                885                 890                 895

Pro Ile Gly Gln Ala Asp Glu Met Gln Arg Tyr Val Glu Glu Asn Gln
            900                 905                 910

Thr Arg Asn Lys His Ile Asn Pro Asn Glu Trp Trp Lys Val Tyr Pro
        915                 920                 925

Ser Ser Val Thr Glu Phe Lys Phe Leu Phe Val Ser Gly His Phe Lys
        930                 935                 940

Gly Asn Tyr Lys Ala Gln Leu Thr Arg Leu Asn His Ile Thr Asn Cys
945                 950                 955                 960

Asn Gly Ala Val Leu Ser Val Glu Glu Leu Leu Ile Gly Gly Glu Met
                965                 970                 975

Ile Lys Ala Gly Thr Leu Thr Leu Glu Glu Val Arg Arg Lys Phe Asn
            980                 985                 990

Asn Gly Glu Ile Asn Phe
        995
```

<210> SEQ ID NO 35
<211> LENGTH: 34
<212> TYPE: PRT
<213> ORGANISM: Homo sapiens
<220> FEATURE:
<221> NAME/KEY: misc_feature
<222> LOCATION: (12)..(13)
<223> OTHER INFORMATION: Xaa can be any naturally occurring amino acid

<400> SEQUENCE: 35

```
Leu Thr Pro Asp Gln Val Val Ala Ile Ala Ser Xaa Xaa Gly Gly Lys
1               5                   10                  15
```

Gln Ala Leu Glu Thr Val Gln Arg Leu Pro Val Leu Cys Gln Asp
            20                  25                  30

His Gly

<210> SEQ ID NO 36
<211> LENGTH: 34
<212> TYPE: PRT
<213> ORGANISM: Homo sapiens
<220> FEATURE:
<221> NAME/KEY: misc_feature
<222> LOCATION: (12)..(13)
<223> OTHER INFORMATION: Xaa can be any naturally occurring amino acid

<400> SEQUENCE: 36

Leu Thr Pro Glu Gln Val Val Ala Ile Ala Ser Xaa Xaa Gly Gly Lys
1               5                   10                  15

Gln Ala Leu Glu Thr Val Gln Arg Leu Pro Val Leu Cys Gln Ala
            20                  25                  30

His Gly

<210> SEQ ID NO 37
<211> LENGTH: 34
<212> TYPE: PRT
<213> ORGANISM: Homo sapiens
<220> FEATURE:
<221> NAME/KEY: misc_feature
<222> LOCATION: (12)..(13)
<223> OTHER INFORMATION: Xaa can be any naturally occurring amino acid

<400> SEQUENCE: 37

Leu Thr Pro Asp Gln Val Val Ala Ile Ala Ser Xaa Xaa Gly Gly Lys
1               5                   10                  15

Gln Ala Leu Glu Thr Val Gln Arg Leu Pro Val Leu Cys Gln Ala
            20                  25                  30

His Gly

<210> SEQ ID NO 38
<211> LENGTH: 34
<212> TYPE: PRT
<213> ORGANISM: Homo sapiens
<220> FEATURE:
<221> NAME/KEY: misc_feature
<222> LOCATION: (12)..(13)
<223> OTHER INFORMATION: Xaa can be any naturally occurring amino acid

<400> SEQUENCE: 38

Leu Thr Pro Ala Gln Val Val Ala Ile Ala Ser Xaa Xaa Gly Gly Lys
1               5                   10                  15

Gln Ala Leu Glu Thr Val Gln Arg Leu Pro Val Leu Cys Gln Asp
            20                  25                  30

His Gly

<210> SEQ ID NO 39
<211> LENGTH: 55
<212> TYPE: DNA
<213> ORGANISM: Artificial Sequence
<220> FEATURE:
<223> OTHER INFORMATION: Synthetic sequence

<400> SEQUENCE: 39
tccattccta tgactgtaga tttttatcag actgaagagc tattgtgtga gtata        55

<210> SEQ ID NO 40

```
<211> LENGTH: 55
<212> TYPE: DNA
<213> ORGANISM: Artificial Sequence
<220> FEATURE:
<223> OTHER INFORMATION: Synthetic sequence

<400> SEQUENCE: 40
aggtaaggat actgacatct aaaatagtct gacttctcga ataacacact catat         55

<210> SEQ ID NO 41
<211> LENGTH: 54
<212> TYPE: DNA
<213> ORGANISM: Artificial Sequence
<220> FEATURE:
<223> OTHER INFORMATION: Synthetic sequence

<400> SEQUENCE: 41
tgaattggga tgctgttttt aggtattcta ttcaaattta ttttactgtc ttta          54

<210> SEQ ID NO 42
<211> LENGTH: 54
<212> TYPE: DNA
<213> ORGANISM: Artificial Sequence
<220> FEATURE:
<223> OTHER INFORMATION: Synthetic sequence

<400> SEQUENCE: 42
acttaaccct acgacaaaaa tccataagat aagtttaaat aaaatgacag aaat          54

<210> SEQ ID NO 43
<211> LENGTH: 52
<212> TYPE: DNA
<213> ORGANISM: Artificial Sequence
<220> FEATURE:
<223> OTHER INFORMATION: Synthetic sequence

<400> SEQUENCE: 43
tatgtacgcc tccctgggct cgggtccggt cgcccctttg cccgcttctg ta            52

<210> SEQ ID NO 44
<211> LENGTH: 52
<212> TYPE: DNA
<213> ORGANISM: Artificial Sequence
<220> FEATURE:
<223> OTHER INFORMATION: Synthetic sequence

<400> SEQUENCE: 44
atacatgcgg agggacccga gcccaggcca gcggggaaac gggcgaagac at            52

<210> SEQ ID NO 45
<211> LENGTH: 55
<212> TYPE: DNA
<213> ORGANISM: Artificial Sequence
<220> FEATURE:
<223> OTHER INFORMATION: Synthetic sequence

<400> SEQUENCE: 45
tcttcaagga cgacggcaac tacaagaccc gcgccgaggt gaagttcgag ggcga         55

<210> SEQ ID NO 46
<211> LENGTH: 55
<212> TYPE: DNA
<213> ORGANISM: Artificial Sequence
<220> FEATURE:
<223> OTHER INFORMATION: Synthetic sequence

<400> SEQUENCE: 46
```
agaagttcct gctgccgttg atgttctggg cgcggctcca cttcaagctc ccgct         55

<210> SEQ ID NO 47
<211> LENGTH: 54
<212> TYPE: DNA
<213> ORGANISM: Artificial Sequence
<220> FEATURE:
<223> OTHER INFORMATION: Synthetic sequence

<400> SEQUENCE: 47
tccattccta tgactgtaga ttttatcaga ctgaagagct attgtgtgag tata          54

<210> SEQ ID NO 48
<211> LENGTH: 54
<212> TYPE: DNA
<213> ORGANISM: Artificial Sequence
<220> FEATURE:
<223> OTHER INFORMATION: Synthetic sequence

<400> SEQUENCE: 48
aggtaaggat actgacatct aaaatagtct gacttctcga taacacactc atat          54

<210> SEQ ID NO 49
<211> LENGTH: 54
<212> TYPE: DNA
<213> ORGANISM: Artificial Sequence
<220> FEATURE:
<223> OTHER INFORMATION: Synthetic sequence

<400> SEQUENCE: 49
tccattccga tgactgtaga ttttatcaga ctgaagagct attgtgtgag tata          54

<210> SEQ ID NO 50
<211> LENGTH: 54
<212> TYPE: DNA
<213> ORGANISM: Artificial Sequence
<220> FEATURE:
<223> OTHER INFORMATION: Synthetic sequence

<400> SEQUENCE: 50
aggtaaggct actgacatct aaaatagtct gacttctcga taacacactc atat          54

<210> SEQ ID NO 51
<211> LENGTH: 54
<212> TYPE: DNA
<213> ORGANISM: Artificial Sequence
<220> FEATURE:
<223> OTHER INFORMATION: Synthetic sequence

<400> SEQUENCE: 51
tccattccga tgactgtaga ttttatcaga ctgaagagct attgagtgag tata          54

<210> SEQ ID NO 52
<211> LENGTH: 54
<212> TYPE: DNA
<213> ORGANISM: Artificial Sequence
<220> FEATURE:
<223> OTHER INFORMATION: Synthetic sequence

<400> SEQUENCE: 52
aggtaaggct actgacatct aaaatagtct gacttctcga taactcactc atat          54

<210> SEQ ID NO 53
<211> LENGTH: 54
<212> TYPE: DNA

```
<213> ORGANISM: Artificial Sequence
<220> FEATURE:
<223> OTHER INFORMATION: Synthetic sequence

<400> SEQUENCE: 53
tctattccga tgactgtaga ttttatcaga ctgaagagct attgagtgac tata        54

<210> SEQ ID NO 54
<211> LENGTH: 54
<212> TYPE: DNA
<213> ORGANISM: Artificial Sequence
<220> FEATURE:
<223> OTHER INFORMATION: Synthetic sequence

<400> SEQUENCE: 54
agataaggct actgacatct aaaatagtct gacttctcga taactcactg atat        54
```

POLYPEPTIDE CONTAINING DNA-BINDING DOMAIN

SEQUENCE LISTING SUBMISSION VIA EFS-WEB

A computer readable text file, entitled "SequenceListing.txt," created on or about May 13, 2016 with a file size of about 46 kb contains the sequence listing for this application and is hereby incorporated by reference in its entirety.

TECHNICAL FIELD

The present invention relates to a polypeptide containing a DNA-binding domain and a function domain. The present invention also relates to a vector comprising a polynucleotide coding for said polypeptide. The present invention further relates to a vector library for preparing said vector. The present invention also relates to a vector set for preparing said vector library. The present application claims the priority based on Japanese patent application No. 2013-166768 filed on Aug. 9, 2013, a whole content of which is incorporated herein by reference.

BACKGROUND ART

For a polypeptide comprising a plurality of nuclease subunits consisting of a DNA-binding domain and a function domain, TALEN (TALE Nuclease), ZFN (Zinc Finger Nuclease) and the like are known (Patent references 1-4, Non-patent references 1-5). For instance, an artificial nuclease is known in which a DNA-cleaving domain is used as a function domain. These artificial nucleases cause cleavage of DNA duplicates by a multimer formed by a plurality of DNA-cleaving domains approaching close together around a binding site of a DNA-binding domain. A DNA-binding domain comprises repetition of plurality of DNA-binding modules and the respective DNA-binding module recognizes a specific base pair in a DNA strand. Thus, by suitably designing DNA-binding modules, it becomes possible to specifically cleave a sequence of interest. By utilizing errors and recombinations that occur when sequence specific cleavage is subject to repair, it is possible to introduce deletion, insertion and mutation of a gene on a genomic DNA. Therefore, these nucleases may be applied for various genetic modifications such as a genome editing (cf. Non-patent reference 6).

Non-patent reference 1 discloses a polypeptide in which a DNA-binding domain and a function domain are linked to each other via a linker of 47 amino acid residues. Non-patent reference 1 discloses a nuclease in which a single amino acid residue in a specific site in a DNA-binding module other than a DNA recognition site is periodically varied for the every four DNA-binding modules used. However, Non-patent reference 1 fails to disclose that the used polypeptide has compatibility between a high level of desired function of a function domain and a high level of specificity of sequence recognition of a DNA binding domain. Non-patent reference 1 also fails to disclose that a plurality of amino resides in a DNA-binding module are periodically varied. Non-patent reference 1 also fails to disclose the significance and the purpose of the periodical variation.

Non-patent reference 2 discloses a polypeptide in which a DNA-binding domain and a function domain are linked to each other via a linker of 63 amino acid residues. Non-patent reference 2 also discloses a polypeptide in which amino acid residue(s) in a DNA-binding module other than those amino acid residues in a DNA recognition site is/are periodically varied for the every four DNA-binding modules used. However, Non-patent reference 2 fails to disclose that the used polypeptide has compatibility between a high level of desired function of a function domain and a high level of specificity of sequence recognition of a DNA-binding domain. Non-patent reference 2 also does not refer to anything about the purpose and the significance of the periodical variation for every four DNA-binding modules.

Non-patent reference 3 discloses a polypeptide in which a DNA-binding domain and a function domain are linked to each other via a linker of 47 amino acid residues. Non-patent reference 3 also discloses a polypeptide in which amino acid residue(s) in a DNA-binding module other than those amino acid residues in a DNA recognition site is/are varied at random for the every DNA-binding modules used. However, Non-patent reference 3 fails to disclose that the used polypeptide has compatibility between a high level of desired function of a function domain and a high level of specificity of sequence recognition of a DNA-binding domain. Non-patent reference 3 also fails to disclose the purpose and the significance of the variation at random. Non-patent reference 3 also fails to disclose the periodical variation for every DNA-binding module.

Non-patent reference 4 discloses a polypeptide in which a DNA-binding domain and a function domain are linked to each other via a linker of 63 amino acid residues. Non-patent reference 5 discloses a polypeptide in which a DNA-binding domain and a function domain are linked to each other via a linker of 47 amino acid residues. However, neither Non-patent reference 4 nor Non-patent reference 5 discloses that the used polypeptide has compatibility between a high level of desired function of a function domain and a high level of specificity of sequence recognition of a DNA-binding domain. Also, neither Non-patent reference 4 nor Non-patent reference 5 discloses the periodical variation for every DNA-binding module.

PATENT REFERENCES

Patent reference 1: WO 2011/072246
Patent reference 2: WO 2011/154393
Patent reference 3: WO 2011/159369
Patent reference 4: WO 2012/093833

NON-PATENT REFERENCES

Non-patent reference 1: Nucleic Acids Res. 2011 November; 39(21):9283-93.
Non-patent reference 2: Nat Biotechnol. 2011 Aug. 5; 29(8): 697-8.
Non-patent reference 3: Nat Biotechnol. 2011 February; 29(2):143-8.
Non-patent reference 4: Nature. 2012 Nov. 1; 491(7422): 114-8.
Non-patent reference 5: Genes Cells. 2013 April; 18(4):315-26.
Non-patent reference 6: Cell.2011 Jul. 22; 146(2):318-31.

DISCLOSURE OF THE INVENTION

Technical Problem to be Solved by the Invention

It is expected that efficiency for obtaining a desired result is improved when a polypeptide comprising a DNA-binding domain with high function of a function domain is used. For instance, in case of an artificial nuclease comprising a DNA-binding domain and a DNA-cleaving domain, it is expected that probability of DNA cleavage is improved to improve efficiency for obtaining cells with a genetic modification of interest when such a nuclease as having a high DNA cleavage activity is used. However, a conventional polypeptide comprising a DNA-binding domain, when showing a high activity of a function domain, is likely to exert a high function also in the region other than a target nucleotide sequence of a DNA-binding domain and thus is not appropriate in view of safety. As such, it was difficult to establish compatibility between a high level of specificity of DNA sequence recognition and a high level of function of a function domain. Besides, cumbersome procedures such as introduction of repetition of DNA-binding modules corresponding to target sequences into a vector are necessary for preparing a polypeptide comprising a DNA-binding domain. Thus, there is a need for a polypeptide that can be prepared with simpler procedures more rapidly.

Therefore, an object of the present invention is to provide a polypeptide, which has compatibility between a high level of function of a function domain and a high level of specificity of DNA sequence recognition, can safely exert desired function with high probability, and can be prepared with simple procedures.

Means for Solving the Problems

The present inventors have earnestly studied to solve the above problems and as a result have found that a polypeptide wherein a DNA-binding domain and a function domain are linked to each other via a polypeptide consisting of 35 to 55 amino acid residues and wherein amino acid residues at two specific sites in a DNA-binding module contained in a DNA-binding domain exhibit a mode of repetition that is different for every four DNA-binding modules has compatibility between a high level of function of a function domain and a high level of specificity of DNA sequence recognition. A vector for expressing said polypeptide could be prepared with simple procedures by using a vector set of specific features and a vector library of specific features.

Thus, in the first aspect, the present invention provides a polypeptide comprising a DNA-binding domain and a function domain, wherein the DNA-binding domain and the function domain are linked to each other via a polypeptide consisting of 35 to 55 amino acid residues, wherein the DNA-binding domain comprises a plurality of DNA-binding modules consecutively from the N-terminus, wherein a combination of an amino acid residue at position x and an amino acid residue at position y in a DNA-binding module at position 4n−3 counted from the N-terminus is the same for any of n, wherein a combination of an amino acid residue at position x and an amino acid residue at position y in a DNA-binding module at position 4n−2 counted from the N-terminus is the same for any of n, wherein a combination of an amino acid residue at position x and an amino acid residue at position y in a DNA-binding module at position 4n−1 counted from the N-terminus is the same for any of n, wherein a combination of an amino acid residue at position x and an amino acid residue at position y in a DNA-binding module at position 4n counted from the N-terminus is the same for any of n, wherein a combination of an amino acid residue at position x and an amino acid residue at position y in a DNA-binding module at position 4n−3 counted from the N-terminus, a combination of an amino acid residue at position x and an amino acid residue at position y in a DNA-binding module at position 4n−2 counted from the N-terminus, a combination of an amino acid residue at position x and an amino acid residue at position y in a DNA-binding module at position 4n−1 counted from the N-terminus, and a combination of an amino acid residue at position x and an amino acid residue at position y in a DNA-binding module at position 4n counted from the N-terminus are different from each other, and wherein n is natural number of 1 to 10, x is natural number of 1 to 40, y is natural number of 1 to 40, and x and y are different natural number from each other.

In the second aspect, the present invention provides the polypeptide of the first aspect wherein the function domain is a DNA-cleaving domain.

In the third aspect, the present invention provides a vector comprising a polynucleotide coding for the polypeptide of the first aspect or the second aspect.

In the fourth aspect, the present invention provides a vector library for preparing the vector of the third aspect, wherein the vector library consists of a plurality of vectors, each of which vector has a first restriction site, a polynucleotide coding for four DNA-binding modules and a second restriction site in this order from the 5'-end, wherein a combination of the first restriction site and the second restriction site is any one of a combination of a restriction site of type A and a restriction site of type B, a combination of a restriction site of type A and a restriction site of type C, a combination of a restriction site of type A and a restriction site of type D, a combination of a restriction site of type A and a restriction site of type E, a combination of a restriction site of type B and a restriction site of type C, a combination of a restriction site of type C and a restriction site of type D, and a combination of a restriction site of type D and a restriction site of type E, wherein each of the restriction sites of types A to E produce different cleaved terminals when cleaved with the same restriction enzyme; and among the four DNA-binding modules, wherein, a combination of an amino acid residue at position x and an amino acid residue at position y in a DNA-binding module at position 1 counted from the 5'-terminus is the same for any of the vectors, wherein a combination of an amino acid residue at position x and an amino acid residue at position y in a DNA-binding module at position 2 counted from the 5'-terminus is the same for any of the vectors, wherein a combination of an amino acid residue at position x and an amino acid residue at position y in a DNA-binding module at position 3 counted from the 5'-terminus is the same for any of the vectors, wherein a combination of an amino acid residue at position x and an amino acid residue at position y in a DNA-binding module at position 4 counted from the 5'-terminus is the same for any of the vectors, and wherein a combination of an amino acid residue at position x and an amino acid residue at position y in a DNA-binding module at position 1 counted from the 5'-terminus, a combination of an amino acid residue at position x and an amino acid residue at position y in a DNA-binding module at position 2 counted from the 5'-terminus, a combination of an amino acid residue at position x and an amino acid residue at position y in a DNA-binding module at position 3 counted from the 5'-terminus, and a combination of an amino acid residue at position x and an amino acid residue at position y in a DNA-binding module at position 4 counted from the 5'-terminus are different from each other, and wherein x is natural number of 1 to 40, y is natural number of 1 to 40, and x and y are different natural number from each other.

Furthermore, in the fifth aspect, the present invention provides a vector set for preparing the vector library of the fourth aspect, wherein the vector set comprises a plurality of vectors, each of which vector comprises a first restriction site, a DNA-binding module and a second restriction site in this order from the 5'-end, wherein the first restriction site and the second restriction site produce different cleaved terminals when cleaved with the same restriction enzyme, wherein a combination of an amino acid residue at position x and an amino acid residue at position y in a DNA-binding module is any of the four different combinations, and wherein x is natural number of 1 to 40, y is natural number of 1 to 40, and x and y are different natural number from each other.

In the sixth aspect, the present invention provides a vector comprising a polynucleotide coding for a polypeptide comprising a DNA-binding domain and a function domain, wherein the DNA-binding domain and the function domain are linked to each other via a polypeptide consisting of 40 to 50 amino acid residues, wherein the DNA-binding domain comprises 16 to 20 DNA-binding modules consisting of 34 amino acid residues consecutively from the N-terminus, wherein a combination of an amino acid residue at position 4 and an amino acid residue at position 32 in a DNA-binding module at position 4n−3 counted from the N-terminus is the same for any of n, wherein a combination of an amino acid residue at position 4 and an amino acid residue at position 32 in a DNA-binding module at position 4n−2 counted from the N-terminus is the same for any of n, wherein a combination of an amino acid residue at position 4 and an amino acid residue at position 32 in a DNA-binding module at position 4n−1 counted from the N-terminus is the same for any of n, wherein a combination of an amino acid residue at position 4 and an amino acid residue at position 32 in a DNA-binding module at position 4n counted from the N-terminus is the same for any of n, wherein a combination of an amino acid residue at position 4 and an amino acid residue at position 32 in a DNA-binding module at position 4n−3 counted from the N-terminus, a combination of an amino acid residue at position 4 and an amino acid residue at position 32 in a DNA-binding module at position 4n−2 counted from the N-terminus, a combination of an amino acid residue at position 4 and an amino acid residue at position 32 in a DNA-binding module at position 4n−1 counted from the N-terminus, and a combination of an amino acid residue at position 4 and an amino acid residue at position 32 in a DNA-binding module at position 4n counted from the N-terminus are different from each other, wherein n is natural number of 1 to 5, and wherein the DNA-binding domain is from TALE.

In the vector, the function domain is preferably a DNA-cleaving domain.

In the seventh aspect, the present invention provides a vector library for preparing the vector as set forth in the sixth aspect above, wherein the vector library consists of a plurality of vectors, each of which vector has a first restriction site, a polynucleotide coding for four DNA-binding modules and a second restriction site in this order from the 5'-end, wherein a combination of the first restriction site and the second restriction site is any one of a combination of a restriction site of type A and a restriction site of type B, a combination of a restriction site of type A and a restriction site of type C, a combination of a restriction site of type A and a restriction site of type D, a combination of a restriction site of type A and a restriction site of type E, a combination of a restriction site of type B and a restriction site of type C, a combination of a restriction site of type C and a restriction site of type D, and a combination of a restriction site of type D and a restriction site of type E, wherein each of the restriction sites of types A to E produce different cleaved terminals when cleaved with the same restriction enzyme; and among the four DNA-binding modules, wherein a combination of an amino acid residue at position 4 and an amino acid residue at position 32 in a DNA-binding module at position 1 counted from the 5'-terminus is the same for any of the vectors, wherein a combination of an amino acid residue at position 4 and an amino acid residue at position 32 in a DNA-binding module at position 2 counted from the 5'-terminus is the same for any of the vectors, wherein a combination of an amino acid residue at position 4 and an amino acid residue at position 32 in a DNA-binding module at position 3 counted from the 5'-terminus is the same for any of the vectors, wherein a combination of an amino acid residue at position 4 and an amino acid residue at position 32 in a DNA-binding module at position 4 counted from the 5'-terminus is the same for any of the vectors, and wherein a combination of an amino acid residue at position 4 and an amino acid residue at position 32 in a DNA-binding module at position 1 counted from the 5'-terminus, a combination of an amino acid residue at position 4 and an amino acid residue at position 32 in a DNA-binding module at position 2 counted from the 5'-terminus, a combination of an amino acid residue at position 4 and an amino acid residue at position 32 in a DNA-binding module at position 3 counted from the 5'-terminus, and a combination of an amino acid residue at position 4 and an amino acid residue at position 32 in a DNA-binding module at position 4 counted from the 5'-terminus are different from each other.

In the eighth aspect, the present invention provides a vector set for preparing the vector library as set forth in the seventh aspect above, wherein the vector set comprises a plurality of vectors, each of which vector comprises a first restriction site, a DNA-binding module and a second restriction site in this order from the 5'-end, wherein the first restriction site and the second restriction site produce different cleaved terminals when cleaved with the same restriction enzyme, wherein the first restriction site and the second restriction site are the ones not cleaved by a restriction enzyme that cleaves the first restriction site and the second restriction site contained in the vectors constituting the vector library as set forth in claim 3, and wherein a combination of an amino acid residue at position 4 and an amino acid residue at position 32 in a DNA-binding module is any of the four different combinations.

In the ninth aspect, the present invention provides a method for preparing a modified cell which comprises introducing the vector as set forth in the sixth aspect above into a cell followed by expression.

In the tenth aspect, the present invention provides a method for preparing a modified cell which comprises introducing the vector as set forth in the seventh aspect above into a cell followed by expression.

In the eleventh aspect, the present invention provides a modified cell produced by the method as set forth in the ninth aspect above.

In the twelfth aspect, the present invention provides a cell with mutation on the genome being introduced produced by the method as set forth in the tenth aspect above.

In the thirteenth aspect, the present invention provides a cell with modification by the vector as set forth in the sixth aspect above.

In the fourteenth aspect, the present invention provides a cell with mutation on the genome by the vector as set forth in the seventh aspect above.

In the fifteenth aspect, the present invention provides a plant or an animal comprising the cell as set forth in any one of the eleventh to fourteenth aspects above.

Effects of the Invention

The polypeptide of the present invention accomplishes a high level of function of a function domain and simultaneously a high level of specificity of DNA sequence recognition. Thus, by introducing a vector comprising a polynucleotide coding for the polypeptide of the present invention into cells, a desired result can be attained safely with high probability. Besides, by using the vector library of the present invention, a vector for expressing a polypeptide that has compatibility between a high level of function of a function domain and a high level of specificity of DNA sequence recognition can be prepared with simple procedures rapidly. Furthermore, by using the vector set of the present invention, the vector library of the present invention can be prepared with simple procedures.

BRIEF DESCRIPTION OF DRAWINGS

FIG. 1 is an illustration showing structural features and process for the preparation of the vector set, the vector library and the vector of the present invention.

FIG. 2 shows an embodiment of an amino acid sequence and a nucleotide sequence of a DNA-binding module contained in the vector set, the vector library and the vector of the present invention.

FIG. 3 shows an embodiment of an amino acid sequence and a nucleotide sequence contained in the vector of the present invention.

FIG. 4A shows structural features of the vectors prepared by the methods of Example 3, and Comparative Examples 1 to 3.

FIG. 4B shows structural features of the vectors prepared by the methods of Example 3, and Comparative Examples 1 to 3.

FIG. 4C shows comparison of sequence specificity of nucleases expressed by a combination of various vectors.

FIGS. 5A and 5B show a design of vectors prepared by the methods of Example 3, and Comparative Examples 1 to 3 (FIG. 5A) and comparison of a level of a DNA cleavage activity of nucleases expressed by these vectors (FIG. 5B).

FIGS. 6A and 6B show a design of vectors prepared by the methods of Example 3, and Comparative Examples 1 to 3 (FIG. 6A) and comparison of sequence specificity of nucleases expressed by these vectors (FIG. 6B).

BEST MODE FOR CARRYING OUT THE INVENTION

In the first aspect, the present invention provides a polypeptide comprising a DNA-binding domain and a function domain. A DNA-binding domain may be derived from TALE (Transcription Activator-Like Effector) of plant pathogen *Xanthomonas*, Zinc finger and the like.

A function domain includes a domain coding for an enzyme, a transcriptional regulatory element, a reporter protein and the like. The enzyme includes a DNA modification enzyme such as recombinase, nuclease, ligase, kinase, phosphatase; and other enzymes such as lactamase and the like. As used herein, a domain coding for nuclease is referred to as a DNA-cleaving domain. The transcriptional regulatory element includes activator, repressor and the like. The reporter protein includes a fluorescent protein such as green fluorescent protein (GFP), humanized Renilla green fluorescent protein (hrGFP), enhanced green fluorescent protein (eGFP), enhanced blue fluorescent protein (eBFP), enhanced cyan fluorescent protein (eCFP), enhanced yellow fluorescent protein (eYFP), red fluorescent protein (RFP or DsRed), mCherry and the like; a bioluminescent protein such as firefly luciferase, Renilla luciferase and the like; an enzyme converting a chemiluminescent substrate such as alkaline phosphatase, peroxidase, chloramphenicol acetyltransferase, β-galactosidase and the like. A DNA-cleaving domain is preferably the one that is close by another DNA-cleaving domain to form a multimer to obtain an improved nuclease activity. Such a DNA-cleaving domain includes those from FokI and the like.

In the first aspect of the polypeptide of the present invention, a DNA-binding domain and a function domain are linked to each other via a polypeptide consisting of 35-55, preferably 40-50, more preferably 45-49, most preferably 47 amino acid residues. A polypeptide through which a DNA-binding domain and a function domain are linked to each other includes, for instance, a polypeptide consisting of the amino acid sequence of from position 754 to position 801 of SEQ ID NO: 34 as well as a polypeptide having sequence identity of 85%, 90%, 95%, or 97% with the amino acid sequence of from position 754 to position 801 of SEQ ID NO: 34.

In the first aspect of the polypeptide of the present invention, a DNA-binding domain comprises a plurality of DNA-binding modules consecutively from the N-terminus. A single DNA-binding module recognizes specifically a single base pair. The number of a DNA-binding module contained in a DNA-binding domain is preferably 8-40, more preferably 12-25, even more preferably 15-20 in view of compatibility between a high level of function of a function domain and a high level of specificity of DNA sequence recognition. A DNA-binding module includes, for instance, TAL effector repeat and the like. The length of a DNA-binding module includes, for instance, 20-45, 30-38, 32-36, or 34. The length of DNA-binding modules contained in a DNA-binding domain is preferably the same for all the DNA-binding modules. A DNA-binding module includes, for instance, a polypeptide consisting of the amino acid sequence of from position 1 to position 34 of SEQ ID NOs:2, 4, 6, 8, 10, 12, 14, 16, 18, 20, 22, 24, 26, 28, 30, or 32. When the amino acid residues at positions 12 and 13 in SEQ ID NOs:2, 4, 6, 8, 10, 12, 14, 16, 18, 20, 22, 24, 26, 28, 30, or 32 are H and D, respectively, said DNA-binding domain recognizes C as a nucleotide. When the amino acid residues at positions 12 and 13 are N and G, respectively, said DNA-binding domain recognizes T as a nucleotide. When the amino acid residues at positions 12 and 13 are N and I, respectively, said DNA-binding domain recognizes A as a nucleotide. When the amino acid residues at positions 12 and 13 are N and N, respectively, said DNA-binding domain recognizes G as a nucleotide. A DNA-binding module includes, for instance, a polypeptide which has sequence identity of 85%, 90%, 95%, or 97% with the amino acid sequence of from position 1 to position 34 of SEQ ID NOs:2, 4, 6, 8, 10, 12, 14, 16, 18, 20, 22, 24, 26, 28, 30, or 32 and which substantially retains the function to recognize a single nucleotide.

In the first aspect of the polypeptide of the present invention, a combination of an amino acid residue at position x and an amino acid residue at position y in a DNA-binding module at position 4n−3 counted from the N-terminus is the same for any of n. A combination of an amino acid residue at position x and an amino acid residue at position y in a DNA-binding module at position 4n−2 counted from the N-terminus is the same for any of n. A combination of an amino acid residue at position x and an amino acid residue at position y in a DNA-binding module at position 4n−1 counted from the N-terminus is the same for any of n. A combination of an amino acid residue at position x and an amino acid residue at position y in a DNA-binding module at position 4n counted from the N-terminus is the same for any of n. In this context, n is natural number of 1 to 10, preferably natural number of 1 to 7, more preferably natural number of 1 to 5 and is preferably natural number that is sufficient for referring to all the DNA-binding modules contained in a DNA-binding domain. In this context, x is natural number of 1 to 40, preferably natural number of 1 to 10, more preferably natural number of 2 to 6, even more preferably natural number of 3 to 5, most preferably natural number of 4. In this context, y is natural number of 1 to 40, preferably natural number of 25 to 40, more preferably natural number of 30 to 36, even more preferably natural number of 31 to 33, most preferably natural number of 32. In this context, x and y are different natural number from each other. The values of x and y may vary depending on the length of a DNA-binding module used. In this context, x preferably represents the number indicating the position corresponding to the amino acid residue at position 4 in a DNA-binding module consisting of 34 amino acid residues whereas y preferably represents the number indicating the position corresponding to the amino acid residue at position 32 in a DNA-binding module consisting of 34 amino acid residues.

In the first aspect of the polypeptide of the present invention, a combination of an amino acid residue at position x and an amino acid residue at position y in a DNA-binding module at position 4n−3 counted from the N-terminus, a combination of an amino acid residue at position x and an amino acid residue at position y in a DNA-binding module at position 4n−2 counted from the N-terminus, a combination of an amino acid residue at position x and an amino acid residue at position y in a DNA-binding module at position 4n−1 counted from the N-terminus, and a combination of an amino acid residue at position x and an amino acid residue at position y in a DNA-binding module at position 4n counted from the N-terminus are different from each other. In this context, n is natural number of 1 to 10, preferably natural number of 1 to 7, more preferably natural number of 1 to 5 and is preferably natural number that is sufficient for referring to all the DNA-binding modules contained in a DNA-binding domain. In this context, x is natural number of 1 to 40, preferably natural number of 1 to 10, more preferably natural number of 2 to 6, even more preferably natural number of 3 to 5, most preferably natural number of 4. In this context, y is natural number of 1 to 40, preferably natural number of 25 to 40, more preferably natural number of 30 to 36, even more preferably natural number of 31 to 33, most preferably natural number of 32. In this context, x and y are different natural number from each other. Preferably, a combination of an amino acid residue at position x and an amino acid residue at position y in a DNA-binding module at position 4n−3 counted from the N-terminus, a combination of an amino acid residue at position x and an amino acid residue at position y in a DNA-binding module at position 4n−2 counted from the N-terminus, and a combination of an amino acid residue at position x and an amino acid residue at position y in a DNA-binding module at position 4n counted from the N-terminus are selected from the group consisting of a combination of D and D, a combination of E and A, a combination of D and A, and a combination of A and D, respectively for x and y in this order.

In the second aspect, the present invention provides the polypeptide of the first aspect wherein the function domain is a DNA-cleaving domain.

In the third aspect, the present invention provides a vector comprising a polynucleotide coding for the polypeptide of the first aspect or the second aspect. A vector includes a plasmid vector, a cosmid vector, a viral vector, an artificial chromosome vector and the like. An artificial chromosome vector includes a yeast artificial chromosome vector (YAC), a bacterial artificial chromosome vector (BAC), a P1 artificial chromosome vector (PAC), a mouse artificial chromosome vector (MAC), and a human artificial chromosome vector (HAC). A component of a vector includes a nucleic acid such as DNA, RNA and the like, a nucleic acid analogue such as GNA, LNA, BNA, PNA, TNA and the like. A vector may be modified with a component other than a nucleic acid such as a saccharide.

By introducing the vector of the third aspect of the present invention into cells and the like for expression, the polypeptide of the first aspect or the second aspect of the present invention can be prepared. Also, by introducing the vector of the third aspect of the present invention into cells and the like for expression, a desired function corresponding to a function domain can be fulfilled in cells such as DNA modification such as DNA recombination, DNA cleavage, etc.; expression of other enzymatic activity such as transcriptional regulation; labelling of a DNA region by a reporter protein. In case that a function domain is a DNA-cleaving domain, by introducing plural, preferably two, of the vectors of the third aspect of the present invention into cells and the like for expression, nucleotide sequence-specific double strand cleavage can be induced on a genomic DNA of the cells where the vector is introduced so that mutation is introduced in the genome of the cells. The source of cells to which the vector of the third aspect of the present invention is introduced includes an animal such as mammal, e.g. *Drosophila*, zebrafish and mouse, a plant such as *Arabidopsis thaliana*, culture cells such as ES cells, iPS cells, and the like.

In the fourth aspect, the present invention provides a vector library for preparing the vector of the third aspect.

The vector library of the fourth aspect of the present invention is composed of a plurality of vectors. The vector library preferably comprises vectors useful for preparing the vector of the third aspect exhaustively with regard to a combination of four kinds of nucleotide which a combination of four DNA-binding modules recognizes. However, as far as the manufacture of the vector of the third aspect is possible, the vector library may comprise vectors not exhaustively. The vector library of the fourth aspect of the present invention comprises vectors for exhaustively constructing the polypeptide of the first aspect or the second aspect of the present invention comprising e.g. 6 to 9, 10 to 13, 14 to 17, or 18 to 21 DNA-binding modules. The polypeptide of the first aspect or the second aspect of the present invention, when having 14 to 21 DNA-binding modules, is particularly excellent in compatibility between a high level of specificity of sequence recognition and a high level of function of a function domain. Thus, such a vector library, though comprising a rather small number of vectors, is excellent as allowing for the manufacture of the polypeptide of the first aspect or the second aspect with high effects by means of simple procedures.

All the vectors constituting the vector library of the fourth aspect of the present invention comprise a first restriction site, a polynucleotide coding for four DNA-binding modules and a second restriction site in this order from the 5'-end.

A combination of a first restriction site and a second restriction site contained in a vector constituting the vector library of the fourth aspect of the present invention is any one of a combination of a restriction site of type A and a restriction site of type B, a combination of a restriction site of type A and a restriction site of type C, a combination of a restriction site of type A and a restriction site of type D, a combination of a restriction site of type A and a restriction site of type E, a combination of a restriction site of type B and a restriction site of type C, a combination of a restriction site of type C and a restriction site of type D, and a combination of a restriction site of type D and a restriction site of type E. Types A to E indicated in relation to a restriction site are used herein for descriptive purposes for showing difference in property of the respective restriction sites. In case that the types are different from each other, property of their restriction sites is different whereas in case that the types are the same, property of their restriction sites is the same. In the vector library of the fourth aspect of the present invention, the restriction sites of type A to type E are cleaved by the same restriction enzyme. Also, the restriction sites of type A to type E are cleaved by the same restriction enzyme to thereby produce cleaved terminals different from each other. Such a restriction site includes the one by a restriction enzyme that cleaves an arbitrary site adjacent to a recognition site of the restriction enzyme, for instance, BsaI, BbsI, BsmBI and the like.

As shown in FIG. 1, STEP 2, for the manufacture of the vector of the third aspect of the present invention comprising 18 to 21 DNA-binding modules, the vector library of the fourth aspect of the present invention comprises a vector wherein a combination of a first restriction site and a second restriction site is a combination of a restriction site of type A and a restriction site of type B, a vector wherein a combination of a first restriction site and a second restriction site is a combination of a restriction site of type B and a restriction site of type C, a vector wherein a combination of a first restriction site and a second restriction site is a combination of a restriction site of type C and a restriction site of type D, and a vector wherein a combination of a first restriction site and a second restriction site is a combination of a restriction site of type D and a restriction site of type E, preferably exhaustively with regard to nucleotides recognized by DNA-binding modules.

Also as shown in FIG. 1, STEP 2, for the manufacture of the vector of the third aspect of the present invention comprising 14 to 17 DNA-binding modules, the vector library of the fourth aspect of the present invention comprises a vector wherein a combination of a first restriction site and a second restriction site is a combination of a restriction site of type A and a restriction site of type C, a vector wherein a combination of a first restriction site and a second restriction site is a combination of a restriction site of type C and a restriction site of type D, and a vector wherein a combination of a first restriction site and a second restriction site is a combination of a restriction site of type D and a restriction site of type E, preferably exhaustively with regard to nucleotides recognized by DNA-binding modules.

Besides, as shown in FIG. 1, STEP 2, for the manufacture of the vector of the third aspect of the present invention comprising 10 to 13 DNA-binding modules, the vector library of the fourth aspect of the present invention comprises a vector wherein a combination of a first restriction site and a second restriction site is a combination of a restriction site of type A and a restriction site of type D, and a vector wherein a combination of a first restriction site and a second restriction site is a combination of a restriction site of type D and a restriction site of type E, preferably exhaustively with regard to nucleotides recognized by DNA-binding modules.

Furthermore, as shown in FIG. 1, STEP 2, for the manufacture of the vector of the third aspect of the present invention comprising 6 to 9 DNA-binding modules, the vector library of the fourth aspect of the present invention comprises a vector wherein a combination of a first restriction site and a second restriction site is a combination of a restriction site of type A and a restriction site of type E, preferably exhaustively with regard to nucleotides recognized by DNA-binding modules.

The vectors constituting the vector library of the fourth aspect of the present invention comprises DNA-binding modules. The length of a DNA-binding module includes, for instance, 30 to 38, 32 to 36, or 34. The length of DNA-binding modules contained in a DNA-binding domain is preferably the same for all the vectors constituting the vector library. Also, the length of DNA-binding modules contained in a DNA-binding domain is preferably the same for all the four DNA-binding modules contained in the vector constituting the vector library. A DNA-binding module includes, for instance, a polypeptide consisting of the amino acid sequence of from position 1 to position 34 of SEQ ID NOs:2, 4, 6, 8, 10, 12, 14, 16, 18, 20, 22, 24, 26, 28, 30, or 32. A DNA-binding module includes, for instance, a polypeptide which has sequence identity of 85%, 90%, 95%, or 97% with the amino acid sequence of from position 1 to position 34 of SEQ ID NOs:2, 4, 6, 8, 10, 12, 14, 16, 18, 20, 22, 24, 26, 28, 30, or 32 and which substantially retains the function to recognize a single nucleotide.

Among the four DNA-binding modules contained in vectors constituting the vector library of the fourth aspect of the present invention, a combination of an amino acid residue at position x and an amino acid residue at position y in a DNA-binding module at position 1 counted from the 5'-terminus is the same for an arbitrary vector constituting the vector library. Likewise, a combination of an amino acid residue at position x and an amino acid residue at position y in a DNA-binding module at position 2 counted from the 5'-terminus is the same for an arbitrary vector constituting the vector library. Also, a combination of an amino acid residue at position x and an amino acid residue at position y in a DNA-binding module at position 3 counted from the 5'-terminus is the same for an arbitrary vector constituting the vector library. Also, a combination of an amino acid residue at position x and an amino acid residue at position y in a DNA-binding module at position 4 counted from the 5'-terminus is the same for an arbitrary vector constituting the vector library. In this context, x is natural number of 1 to 40, preferably natural number of 1 to 10, more preferably natural number of 2 to 6, even more preferably natural number of 3 to 5, most preferably natural number of 4. In this context, y is natural number of 1 to 40, preferably natural number of 25 to 40, more preferably natural number of 30 to 36, even more preferably natural number of 31 to 33, most preferably natural number of 32. In this context, x and y are different natural number from each other. The values of x and y may vary depending on the length of a DNA-binding module used. In this context, x preferably represents the number indicating the position corresponding to the amino acid residue at position 4 in a DNA-binding module consisting of 34 amino acid residues whereas y preferably represents the number indicating the position corresponding to the amino acid residue at position 32 in a DNA-binding module consisting of 34 amino acid residues.

Among the four DNA-binding modules contained in vectors constituting the vector library of the fourth aspect of the present invention, a combination of an amino acid residue at position x and an amino acid residue at position y in a DNA-binding module at position 1 counted from the 5'-terminus, a combination of an amino acid residue at position x and an amino acid residue at position y in a DNA-binding module at position 2 counted from the 5'-terminus, a combination of an amino acid residue at position x and an amino acid residue at position y in a DNA-binding module at position 3 counted from the 5'-terminus, and a combination of an amino acid residue at position x and an amino acid residue at position y in a DNA-binding module at position 4 counted from the 5'-terminus, are different from each other. In this context, x is natural number of 1 to 40, preferably natural number of 1 to 10, more preferably natural number of 2 to 6, even more preferably natural number of 3 to 5, most preferably natural number of 4. In this context, y is natural number of 1 to 40, preferably natural number of 25 to 40, more preferably natural number of 30 to 36, even more preferably natural number of 31 to 33, most preferably natural number of 32. In this context, x and y are different natural number from each other. The values of x and y may be for instance those as described above. Preferably, a combination of an amino acid residue at position x and an amino acid residue at position y in a DNA-binding module at position 1 counted from the 5'-terminus is D and D, a combination of an amino acid residue at position x and an amino acid residue at position y in a DNA-binding module at position 2 counted from the 5'-terminus is E and A, a combination of an amino acid residue at position x and an amino acid residue at position y in a DNA-binding module at position 3 counted from the 5'-terminus is D and A, and a combination of an amino acid residue at position x and an amino acid residue at position y in a DNA-binding module at position 4 counted from the 5'-terminus is A and D, respectively for x and y in this order.

By using the vector library of the fourth aspect of the present invention, the vector of the third aspect of the present invention can be prepared with simple procedures. Specifically, vectors corresponding to the sequence of DNA-binding modules contained in the vector of the third aspect of the present invention are selected from the vector library of the fourth aspect of the present invention, the selected vectors are digested with restriction enzymes that cleave restriction sites of types A to E and the vector fragments obtained by digestion are linked together to prepare the vector of the third aspect of the present invention. All the vectors constituting the vector library of the fourth aspect of the present invention have two restriction sites, which are cleaved by the same restriction enzyme and produce cleaved terminals different from each other as a consequence of cleavage by said enzyme. Thus, for the manufacture of the vector of the third aspect of the present invention, digestion of the selected vectors and ligation of the vector fragments can be performed in one and the same reaction solution, respectively. Therefore, by using the vector library of the fourth aspect of the present invention, the vector of the third aspect of the present invention can be prepared with quite simple procedures.

In the fifth aspect, the present invention provides a vector set for preparing the vector library of the fourth aspect.

The vector set of the fifth aspect of the present invention comprises a plurality of vectors. The vector set preferably comprises vectors useful for preparing the vector library of the fourth aspect exhaustively. However, as far as the manufacture of the vector library of the fourth aspect is possible, the vector set may comprise vectors not exhaustively.

All the vectors contained in the vector set of the fifth aspect of the present invention comprises a first restriction site, a DNA-binding module and a second restriction site in this order from the 5'-end. The first restriction site and the second restriction site are preferably the ones not cleaved by a restriction enzyme that cleaves the first restriction site and the second restriction site contained in the vectors constituting the vector library of the fourth aspect of the present invention. In this regard, the vector of the third aspect can be prepared from the vector library of the fourth aspect with simpler procedures.

The length of a DNA-binding module in the vector contained in the vector set of the fifth aspect of the present invention is preferably the same for all the vectors contained in the vector set. A DNA-binding module includes, for instance, a polypeptide consisting of the amino acid sequence of from position 1 to position 34 of SEQ ID NOs:2, 4, 6, 8, 10, 12, 14, 16, 18, 20, 22, 24, 26, 28, 30, or 32. A DNA-binding module includes, for instance, a polypeptide which has sequence identity of 85%, 90%, 95%, or 97% with the amino acid sequence of from position 1 to position 34 of SEQ ID NOs:2, 4, 6, 8, 10, 12, 14, 16, 18, 20, 22, 24, 26, 28, 30, or 32 and which substantially retains the function to recognize a single nucleotide.

The first restriction site and the second restriction site in the vector contained in the vector set of the fifth aspect of the present invention are cleaved by the same restriction enzyme. The first restriction site and the second restriction site are also cleaved by the same restriction enzyme to thereby produce cleaved terminals different from each other. Such a restriction site includes the one by a restriction enzyme that cleaves an arbitrary site adjacent to a recognition site of the restriction enzyme, for instance, BsaI, BbsI, BsmBI and the like.

A combination of an amino acid residue at position x and an amino acid residue at position y in a DNA-binding module in the vector contained in the vector set of the fifth aspect of the present invention is any one of four different combinations. The four different combinations of an amino acid residue at position x and an amino acid residue at position y includes, for instance, a combination of D and D, a combination of E and A, a combination of D and A, and a combination of A and D, for x and y in this order. In this context, x is natural number of 1 to 40, preferably natural number of 1 to 10, more preferably natural number of 2 to 6, even more preferably natural number of 3 to 5, most preferably natural number of 4. In this context, y is natural number of 1 to 40, preferably natural number of 25 to 40, more preferably natural number of 30 to 36, even more preferably natural number of 31 to 33, most preferably natural number of 32. In this context, x and y are different natural number from each other. The values of x and y may vary depending on the length of a DNA-binding module used. In this context, x preferably represents the number indicating the position corresponding to the amino acid residue at position 4 in a DNA-binding module consisting of 34 amino acid residues whereas y preferably represents the number indicating the position corresponding to the amino acid residue at position 32 in a DNA-binding module consisting of 34 amino acid residues.

The vectors contained in the vector set of the fifth aspect of the present invention include a vector in which a combination of the first restriction site and the second restriction site is a combination of a type α restriction site and a type β restriction site and a DNA-binding module recognizes nucleotide of A, T, G, or C; a vector in which a combination of the first restriction site and the second restriction site is a combination of a type β restriction site and a type γ restriction site and a DNA-binding module recognizes nucleotide of A, T, G, or C; a vector in which a combination of the first restriction site and the second restriction site is a combination of a type γ restriction site and a type δ restriction site and a DNA-binding module recognizes nucleotide of A, T, G, or C; a vector in which a combination of the first restriction site and the second restriction site is a combination of a type δ restriction site and a type ε restriction site and a DNA-binding module recognizes nucleotide of A, T, G, or C. In this context, types α to δ of the restriction site as used herein are expediently set for showing difference in property of the restriction site, denoting that different types of the restriction site are different in their property from each other whereas the same types of the restriction site are common in their property. The vector set of the fifth aspect of the present invention preferably include all the vectors mentioned above. In this case, every mode of the vector library of the fourth aspect of the present invention can be prepared.

By using the vector set of the fifth aspect of the present invention, the vector library of the fourth aspect of the present invention can be prepared with simple procedures. Specifically, four vectors are selected from the vector set of the fifth aspect of the present invention based on a combination of the four DNA-binding modules contained in vectors constituting the vector library of the fourth aspect of the present invention, the selected vectors are digested with a restriction enzyme that cleaves the first restriction site and the second restriction site and the vector fragments obtained by digestion are linked together to prepare the vector library of the fourth aspect of the present invention. All the vectors contained in the vector set of the fifth aspect of the present invention have two restriction sites, which are cleaved by the same restriction enzyme and produce cleaved terminals different from each other as a consequence of cleavage by said enzyme. Thus, for the manufacture of the vector library of the fourth aspect of the present invention, digestion of the selected vectors and ligation of the vector fragments can be performed in one and the same reaction solution, respectively. Therefore, by using the vector set of the fifth aspect of the present invention, the vector library of the fourth aspect of the present invention can be prepared with quite simple procedures.

EXAMPLES

The present invention is further explained in more detail by means of the following Examples but is not limited thereto.

Example 1: Preparation of Vector Set

The nucleotide sequence shown in FIG. 2 with addition at both ends of the recognition site of restriction enzyme BsaI was prepared by artificial gene synthesis and inserted into pBluescript SK vector to prepare a vector set (p1HD-p4HD, p1NG-p4NG, p1NI-p4NI, p1NN-p4NN) for use in STEP 1 of FIG. 1.

Example 2: Preparation of Vector Library

Using pFUS_B6 vector (Addgene) as a template, pFUS2 vector shown in STEP 1 of FIG. 1 was prepared by In-Fusion cloning (Clontech). As shown in STEP 1 of FIG. 1, using the prepared pFUS2 vector and the vector set prepared in Example 1, the Golden Gate reaction was performed to prepare a vector library.

Example 3: Preparation of TALEN Expression Vector

Figure 3:
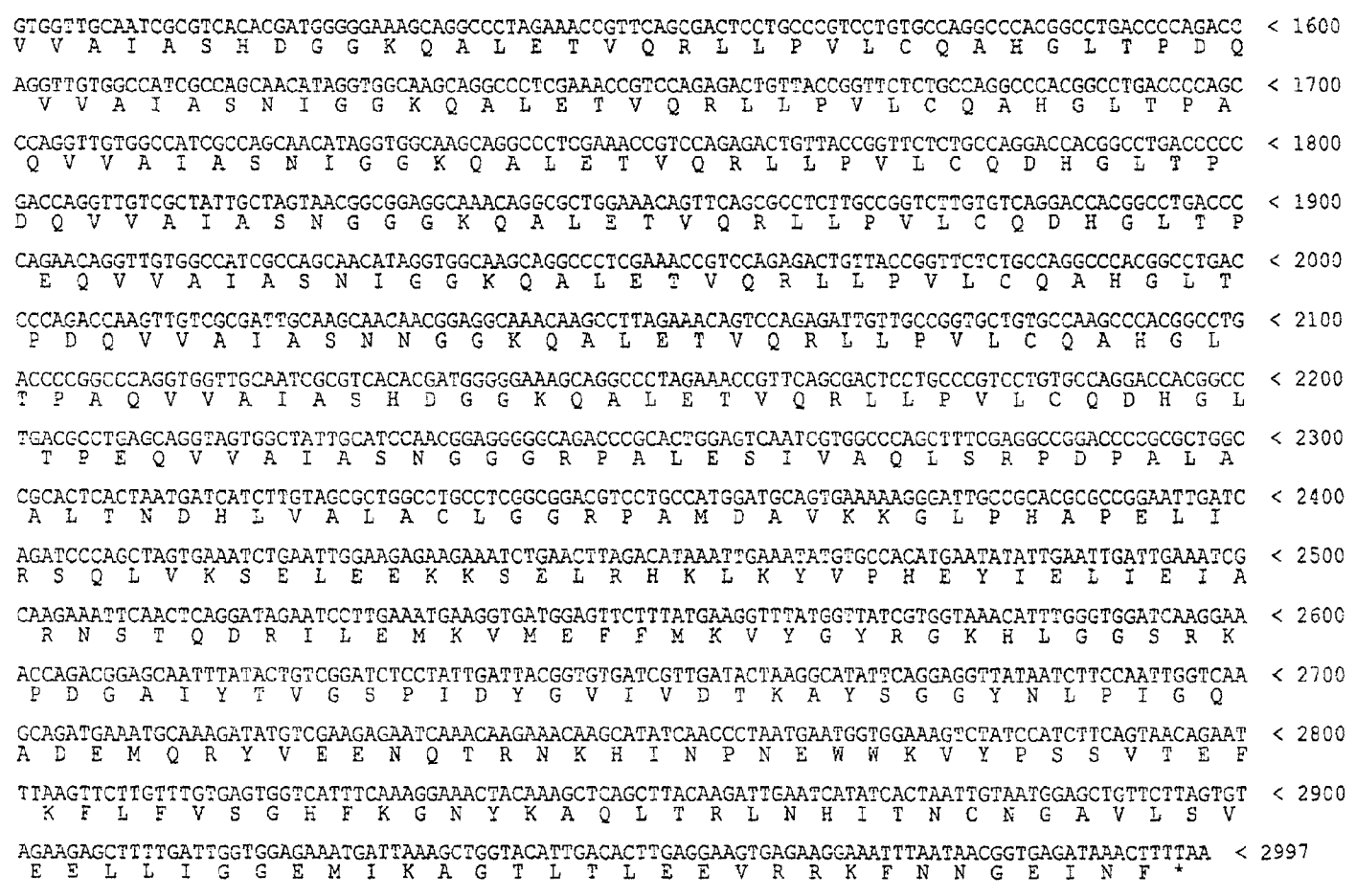

Using pTALEN_v2 and pcDNA-TAL-NC2 (both Addgene), In-Fusion cloning was performed, a BsmBI site adjacent sequence for incorporating modules was prepared by In-Fusion cloning, and a globin leader sequence was introduced upstream the initiation codon by In-Fusion cloning to prepare ptCMV vectors as shown in FIG. 1, STEP 2. Using the prepared ptCMV vectors, the vector library prepared in Example 2, and the vectors contained in Golden Gate TALEN and TAL Effector Kit, Yamamoto Lab TALEN Accessory Pack (both Addgene), DNA-binding domains were inserted by Golden Gate procedure as shown in FIG. 1, STEP 2 to prepare TALEN expression vectors. The ptCMV vector was used in which the number of amino acid residues of a region adjacent to the N-terminus of DNA-binding domain (TALEN-N') is 153 and the number of amino acid residues of a region franked by the C-terminus of DNA-binding domain and a DNA-cleaving domain (TALEN-C') is 47. FIG. 3 shows the nucleotide and amino acid sequences of an example of TALEN prepared.

As shown in FIG. 3, the amino acid residues at position 4 and at position 32 of DNA-binding modules (34 amino acid residues in total) in the TALEN expression vector of Example 3 were different from each other among DNA-binding modules at position 4n–3, at position 4n–2, at position 4n–1 and at position 4n (n is natural number). The amino acid residues at position 4 and at position 32 in DNA-binding modules at position 4n–3 (n is natural number) were common among the respective DNA-binding modules. The same was applied to DNA-binding modules at position 4n–3, at position 4n–2, at position 4n–1 and at position 4n (n is natural number). As such, by using the vector set of Example 1 and the vector library of Example 2, the TALEN expression vectors could be prepared with a repetitive fashion for every four DNA-binding modules.

Comparative Example 1: Preparation of TALEN Expression Vector

The Golden Gate reaction was performed as described in Example 2 except that pHD1-6, pNG1-6, pNI1-6, pNN1-6 contained in Golden Gate TALEN and TAL Effector Kit (Addgene) was used in place of the vector set prepared in Example 1 and that Yamamoto Lab TALEN Accessory Pack (Addgene) was used as pFUS vector for use in the reaction, to prepare a vector library. Using the prepared vector library, the Golden Gate reaction was performed as described in Example 3 to prepare the TALEN expression vectors.

Comparative Example 2: Preparation of TALEN Expression Vector

The procedures of Example 3 were carried out except that the ptCMV vector was used in which the number of amino acid residues of a region adjacent to the N-terminus of DNA-binding domain (TALEN-N') is 136 and the number of amino acid residues of a region franked by the C-terminus of DNA-binding domain and a DNA-cleaving domain (TALEN-C') is 63, to prepare TALEN expression vectors.

Comparative Example 3: Preparation of TALEN Expression Vector

The procedures of Comparative Example 1 were carried out except that the ptCMV vector was used in which the number of amino acid residues of a region adjacent to the N-terminus of DNA-binding domain (TALEN-N') is 136 and the number of amino acid residues of a region franked by the C-terminus of DNA-binding domain and a DNA-cleaving domain (TALEN-C') is 63, to prepare TALEN expression vectors.

Test Example 1: Assessment of Recognition Specificity of TALEN

The TALEN expression vectors (L14 to L20 and R14 to R20) recognizing the sites indicated in FIG. 4B were prepared as in Example 3 or in Comparative Examples 1 to 3. Each one from L14 to L20 and from R14 to R20 as prepared were combined together as shown in FIG. 4C to give right and left TALEN expression vectors. Using the sequences shown in FIG. 4B as a target sequence for TALEN, Single Strand Annealing Assay (cf. Non-patent reference 5) was conducted with HEK293T cell to assess the TALEN activity.

Specifically, Single Strand Annealing Assay was performed as described below. First, a reporter vector was prepared in which a target sequence of TALEN of interest was inserted into a reporter vector (pGL4-SSA; Addgene) wherein a segmented firefly luciferase gene was linked downstream CMV promoter. The target sequence of TALEN was prepared by annealing synthetic oligonucleotides and was inserted into pGL4-SSA vector treated with BsaI using Ligation-Convenience Kit (NIPPON GENE CO., LTD.). Then, the prepared reporter vector together with the TALEN expression vector and pRL-CMV vector (Promega), which is an expression vector of Renilla luciferase, were introduced into HEK293T cells on 96-well plate by lipofectin procedure. After culture for 24 hours, the reporter activity was measured using Dual-Glo Luciferase Assay System (Promega). An amount of DNA introduced is each 200 ng for the right and left TALEN expression vectors, 100 ng for the reporter vector, and 20 ng for the pRL-CMV vector.

Measurement of chemoluminescence was done with TriStar LB 941 plate reader (Berthold Japan K.K.).

FIG. 4C shows relative values of the reporter activity for the respective combinations of the right and left TALEN expression vectors in Example 3 and Comparative Examples 1 to 3 in comparison with a combination of L20 and R17 in Comparative Example 1. Table of FIG. 4B shows the length (the number of nucleotides) of the spacer region franked by the right and left TALEN recognition sites for the respective combinations of the right and left TALEN expression vectors.

As shown in FIG. 4C, in case of Example 3 and Comparative Example 1, a specifically higher activity was obtained only for the limited cases of 12 to 15 of the length of the spacer region, demonstrating that specific cleavage is possible for the limited spacer region. On the other hand, in case of Comparative Example 2 and Comparative Example 3, the level of the activity has no relevance with the length of the spacer region, demonstrating that the possibility is high that sequences with different length of the spacer region are recognized and cleaved. It was thus demonstrated that, by using the TALEN expression vectors of Example 3, efficient DNA cleavage can be conducted with less non-specific cleavage of sequences with different length of the spacer region.

Test Example 2: Assessment of Activity of TALEN

A pair of the right and left TALEN expression vectors that recognize the site shown in FIG. 5A (ATM (L17 for the left, R17 for the right), APC (L17 for the left, R17 for the right) and eGFP (L20 for the left, R18 for the right)) were prepared as in Example 3 or Comparative Examples 1 to 3. Using a pair of the right and left prepared by the respective procedures as the right and left TALEN expression vectors, Single Strand Annealing Assay (Non-patent reference 5) was performed with HEK293T cells as in Test Example 1 using the sequence shown in FIG. 5A as a targeting sequence of TALEN to assess the activity of TALEN.

The results are shown in FIG. 5B in which the axis of ordinate indicates relative values of the reporter activity in comparison with a combination of L20 and R17 of Comparative Example 1 prepared in Test Example 1. As shown in FIG. 5B, in case of Example 3, a higher DNA cleavage activity of TALEN was observed for any of ATM, APC and eGPF as compared to Comparative Example 1. This proved that the repetitive structure of the DNA-binding modules in accordance with the present invention renders the DNA cleavage activity of TALEN be improved.

Test Example 3: Assessment of Recognition Specificity of TALEN

A pair of the right and left TALEN expression vectors that recognize the site shown in FIG. 6A (L19 for the left, R18 for the right) were prepared as in Example 3 or Comparative Examples 1 to 3. Using a pair of the right and left prepared by the respective procedures as the right and left TALEN expression vectors, Single Strand Annealing Assay (Non-patent reference 5) was performed with HEK293T cells as in Test Example 1 using the sequence shown in FIG. 6A (no mismatches, 1 left mismatch and 0 right mismatch (L:1 mismatch/R:0 mismatch), 1 left mismatch and 1 right mismatch (L:1 mismatch/R:1 mismatch), or 2 left mismatches and 2 right mismatches (L:2 mismatches/R:2 mismatches)) as a targeting sequence of TALEN to assess the activity of TALEN. In case that the respective sequences shown in FIG.

6A are used as a targeting sequence of TALEN, mismatch occurs at lower cases in FIG. 6A and thus the level of recognition specificity of TALEN used can be compared by comparing the results of TALEN activity assessment of the targeting sequence of TALEN used.

The results are shown in FIG. 6B in which the axis of ordinate indicates relative values of the measurement of the firefly luciferase activity divided by the measurement of the Renilla luciferase activity. As shown in FIG. 6B, in case that the TALEN expression vectors of Comparative Example 2 were used, even in case of the sequence of 2 left mismatches and 2 right mismatches, a high activity was observed and thus the recognition specificity of the TALEN expression vectors of Comparative Example 2 was low. On the other hand, in case that the TALEN expression vectors of Example 3 were used, in case of the sequence of 2 left mismatches and 2 right mismatches, almost complete loss of the activity was observed. This proved that the TALEN expression vectors of Example 3 can afford to DNA cleavage with high specificity while maintaining a high cleavage activity as shown in Comparative Example 2. Therefore, it was found that a target DNA of interest can be cleaved safely with high probability by using the TALEN expression vectors of Example 3.

INDUSTRIAL APPLICABILITY

The present invention is useful e.g. for production of a variety of substance by genetic engineering technique and can widely be used in the field of medicine, engineering and agriculture.

The invention claimed is:

1. A vector comprising a polynucleotide coding for a polypeptide comprising a DNA-binding domain and a functional domain,
   wherein in the polypeptide, a linker domain between the DNA-binding domain and the functional domain consists of an amino acid sequence having at least 85% sequence identity with the amino acid sequence from position 754 to position 801 of SEQ ID NO: 34,
   the DNA-binding domain comprises consecutive 16 to 20 DNA-binding modules, each of which consists of 34 amino acid residues, in which
      module set 1 consists of 1st, 5th, 9th, 13th and 17th DNA-binding modules from the N-terminus of the DNA-binding domain, and each module of the module set 1 comprises amino acid combination 1 for an amino acid residue at position 4 and an amino acid residue at position 32;
      module set 2 consists of 2nd, 6th, 10th, 14th and 18th DNA-binding modules from the N-terminus of the DNA-binding domain, and each module of the module set 2 comprises amino acid combination 2 for an amino acid residue at position 4 and an amino acid residue at position 32;
      module set 3 consists of 3rd, 7th, 11th, 15th and 19th DNA-binding modules from the N-terminus of the DNA-binding domain, and each module of the module set 3 comprises amino acid combination 3 for an amino acid residue at position 4 and an amino acid residue at position 32;
      module set 4 consists of 4th, 8th, 12th, 16th and 20th DNA-binding modules from the N-terminus of the DNA-binding domain, and each module of the module set 4 comprises amino acid combination 4 for an amino acid residue at position 4 and an amino acid residue at position 32; and
      each of the amino acid combinations 1 to 4 is different from the other combinations;
   the DNA-binding domain has no more than 20 amino acids at the C-terminus of said consecutive 16 to 20 DNA-binding modules, and
   the DNA-binding domain is from a Transcription Activator-Like Effector (TALE).

2. The vector according to claim 1, wherein the functional domain is a DNA-cleaving domain.

3. The vector according to claim 1, wherein each of the combinations 1 to 4 is selected from the group consisting of (i) amino acids D and D; (ii) amino acids E and A; (iii) amino acids D and A; and (iv) amino acids A and D for the amino acid residue at position 4 and the amino acid residue at position 32, respectively.

4. The vector according to claim 1, wherein the linker domain between the DNA-binding domain and the DNA-cleaving domain consists of the amino acid sequence from position 754 to position 801 of SEQ ID NO: 34.

5. The vector according to claim 1, wherein the linker domain between the DNA-binding domain and the DNA-cleaving domain consists of an amino acid sequence having at least 95% sequence identity with the amino acid sequence from position 754 to position 801 of SEQ ID NO: 34.

6. The vector according to claim 1, wherein the linker domain between the DNA-binding domain and the DNA-cleaving domain consists of an amino acid sequence having at least 97% sequence identity with the amino acid sequence from position 754 to position 801 of SEQ ID NO: 34.

7. The vector according to claim 1, wherein the functional domain comprises a DNA-cleaving domain from FokI.

8. The vector according to claim 1, wherein the DNA-binding domain comprises 16 consecutive DNA-binding modules.

9. The vector according to claim 1, wherein the DNA-binding domain comprises 20 consecutive DNA-binding modules.

10. The vector according to claim 1, wherein the 16 to 20 consecutive DNA-binding modules comprise at least one module having a sequence having at least 85% sequence identity with an amino acid sequence selected from the group consisting of SEQ ID NO: 2, 4, 6, 8, 10, 12, 14, 16, 18, 20, 22, 24, 26, 28, 30, and 32.

11. The vector according to claim 1, wherein the 16 to 20 consecutive DNA-binding modules comprise at least one module having a sequence selected from the group consisting of SEQ ID NO: 2, 4, 6, 8, 10, 12, 14, 16, 18, 20, 22, 24, 26, 28, 30, and 32.

12. The vector according to claim 1, wherein the 16 to 20 consecutive DNA-binding modules comprise at least 16 modules having amino acid sequences having at least 85% sequence identity with the amino acid sequences of SEQ ID NO: 2, 4, 6, 8, 10, 12, 14, 16, 18, 20, 22, 24, 26, 28, 30, and 32.

13. The vector according to claim 1, wherein the 16 to 20 consecutive DNA-binding modules comprise at least 16 modules having the amino acid sequences of SEQ ID NO: 2, 4, 6, 8, 10, 12, 14, 16, 18, 20, 22, 24, 26, 28, 30, and 32.

14. The vector according to claim 1, wherein the 16 to 20 consecutive DNA-binding modules consists of 16 modules having amino acid sequences of SEQ ID NO: 2, 4, 6, 8, 10, 12, 14, 16, 18, 20, 22, 24, 26, 28, 30, and 32.

15. The vector according to claim 1, wherein the DNA-binding domain consists of 20 amino acids at the C-terminus of said consecutive 16 to 20 DNA-binding modules.

16. The vector according to claim 1, wherein
the functional domain is a DNA-cleaving domain;
each of the combinations 1 to 4 is selected from the group consisting of (i) amino acids D and D; (ii) amino acids E and A; (iii) amino acids D and A; and (iv) amino acids A and D for the amino acid residue at position 4 and the amino acid residue at position 32, respectively;
the linker domain between the DNA-binding domain and the DNA-cleaving domain consists of the amino acid sequence from position 754 to position 801 of SEQ ID NO: 34; and
the 16 to 20 consecutive DNA-binding modules comprise at least 16 modules having the amino acid sequences of SEQ ID NO: 2, 4, 6, 8, 10, 12, 14, 16, 18, 20, 22, 24, 26, 28, 30, and 32.

17. The vector according to claim 16, wherein the functional domain comprises a DNA-cleaving domain from FokI.

18. The vector according to claim 16, wherein the 16 to 20 consecutive DNA-binding modules consists of 16 modules having amino acid sequences of SEQ ID NO: 2, 4, 6, 8, 10, 12, 14, 16, 18, 20, 22, 24, 26, 28, 30, and 32.

19. The vector according to claim 16, wherein the DNA-binding domain consists of 20 amino acids at the C-terminus of said consecutive 16 to 20 DNA-binding modules.

20. The vector according to claim 16, wherein
the functional domain comprises a DNA-cleaving domain from FokI,
the 16 to 20 consecutive DNA-binding modules consists of 16 modules having amino acid sequences of SEQ ID NO: 2, 4, 6, 8, 10, 12, 14, 16, 18, 20, 22, 24, 26, 28, 30, and 32, and
the DNA-binding domain consists of 20 amino acids at the C-terminus of said consecutive 16 to 20 DNA-binding modules.

* * * * *